US006812335B1

(12) United States Patent
Goetzl et al.

(10) Patent No.: US 6,812,335 B1
(45) Date of Patent: Nov. 2, 2004

(54) HUMAN POLYPEPTIDE RECEPTORS FOR LYSOPHOSPHOLIPIDS AND SPHINGOLIPIDS AND NUCLEIC ACIDS ENCODING THE SAME

(75) Inventors: Edward Goetzl, San Mateo, CA (US); Songzhu An, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/274,752

(22) Filed: Mar. 23, 1999

(51) Int. Cl.$^7$ .......................... C07H 21/04; C07H 1/00; C07H 5/04; C07H 5/06; C08B 37/00
(52) U.S. Cl. ..................... 536/23.5; 536/1; 536/1.11; 536/18.7; 536/22.1; 536/23.1; 435/69.1; 435/325; 530/300; 530/350
(58) Field of Search .................. 435/69.1, 325; 530/350, 300; 536/1, 1.11, 18.7, 22.1, 23.1, 23.5

(56) References Cited

U.S. PATENT DOCUMENTS

| 5,856,443 A | * | 1/1999 | MacLennan |
| 5,912,144 A | | 6/1999 | Au-Young et al. |
| 6,020,158 A | * | 2/2000 | Munroe et al. |
| 6,057,126 A | | 5/2000 | Munroe et al. |

FOREIGN PATENT DOCUMENTS

| EP | 1149907 | 10/2001 |
| WO | WO 9700952 | 1/1997 |
| WO | WO 9848016 | 10/1998 |
| WO | WO 9853062 | 11/1998 |
| WO | WO 00/019513 | 4/1999 |
| WO | 99/33972 | 7/1999 |
| WO | WO 9935106 | 7/1999 |
| WO | 99/35259 | 7/1999 |
| WO | WO 0011166 | 1/2000 |
| WO | WO 0014233 | 3/2000 |
| WO | WO 0015784 | 3/2000 |
| WO | WO 0111022 | 2/2001 |
| WO | WO 0169252 | 9/2001 |
| WO | WO 0181573 | 11/2001 |
| WO | WO 0206446 | 1/2002 |

OTHER PUBLICATIONS

MacLennan et al. Cloning and Characterization of a putative G–protein coupled receptor potentially involved in development. Molecular and Cellular Neurosciences 5:201–209, 1994.*
Lazar et al. Transforming Growth Factor alpha: Mutation of Aspartic Acid 47 and Leucine 48 Results in Different Biological Activities. Molecular and Cellular Biology 8(3):1247–1252, Mar. 1988.*
Nucleic acid database sheet, Accession No. Af011466, Jul. 29, 1998.*
Nucleic acid/amino acid database sheet, Accession AF011466, Jul. 29, 1998.*
Nucleic acid database sheet, Accession No. AF034780, Jan. 1, 1999.*
Nucleic acid/amino acid database sheet, Accession No. AF034780, Jan. 1, 1999.*
Nucleic acid database sheet for Sequence 1 from U.S. Patent No. 5,856,443 (filed Dec. 6, 1996).*
Amino acid database sheet for Sequence 2 from U.S. Patent No. 5,856,443 (filed Dec. 6, 1996).*
Nucleic acid/ amino acid database sheet for U.S. Patent No. 6020158, filed May 22, 1997.*
Nucleic acid database sheet for U.S. Patent No. 6,020,158 filed May 22, 1997.*
Bork et al. Go hunting in sequence databases but watch out for the traps. Trends in Genetics 12(10):425–427, Oct. 1996.*
Doerks et al. Protein annotation: detective work for function prediction. Trends in Genetics 14(6): 248–250, Jun. 1998.*
Bowie et al. Deciphering the Message in Protein Sequences: Tolerance to Amino Acid Substitutions. Science 247:1306–1310, Mar. 16, 1990.*
Brenner, Steven. Errors in genome annotation. Trends in Genetics 15(4): 132 and 133, Apr. 1999.*
Smith and Zhang. The challenge of genome sequence annotation or "The devil is in the details". Nature Biotechnology 15:1222 and 1223, Nov. 1997.*
Bork, Peer. Powers and Pitfalls in Sequence Analysis: The 70% Hurdle. Genome Research 10:398–400, 2000.*
Skolnick and Fetrow. From genes to protein structure and function: novel applications of computational approaches in the genomic era. TIBTECH 18:34–39, Jan. 2000.*
Goetzl et al., "Lysophosphatidic Acid and Sphingosine 1–Phosphate Protection of T Cells from Apoptosis in Association with Suppression of Bax," J Immunol. Feb. 15, 1999; 162(4):2049–56.
EST IMAGE Clone 755526. May 12, 1997.
GenBank Accession No. 22136434. Jun. 24, 1997.
GenBank Accession No. 4090955. Jan. 1, 1999.
An et al., "Molecular Cloning of the Human Edg2 Protein and Its Identification as a Functional Cellular Receptor for Lysophosphatidic Acid," *Biomchemical and Biophysical Research Communications,* 231:619–622 (1997).
An et al., "Identification of cDNA's Encoding two G Protein–coupled receptors for Lysophingolipids," *FEBS,* 417:279–282 (1997).
An et al., "Characterization of a Novel Subtype of Human G Protein–Coupled Receptor for Lysophosphatidic Acid," *Journal Biol. Chem.,* 273(14):7906–7910 (1998).
An et al., "Signaling Mechanisms and Molecular Characteristics of G Protein–Coupled Receptors for Lysophosphatidic Acid and Sphingosine 1–Phosphate," *Journal of Cellular Biochemistry Supplement,* 30/31:147–157 (1998).
An et al., "Recombinant Human G Protein–Coupled Lysophosphatic Acid Receptors Mediate Intracellular Calcium Mobilzation," *Molecular Pharmacology,* 54:881–888 (1998).

* cited by examiner

Primary Examiner—Alana M. Harris
(74) Attorney, Agent, or Firm—Ginger R. Dreger, Esq.; Heller Ehrman White & McAuliffe, LLP

(57) ABSTRACT

Human Edg4 and Edg5 polypeptides and their respective amino acid and nucleic acid sequences are provided for use in investigating cytoprotection, apoptosis, cellular proliferation, and other biological pathways in which phospholipid mediators are implicated.

16 Claims, 2 Drawing Sheets

FIGURE 1: EDG4 AMINO ACID SEQUENCE

```
1                   10                  20                  30                  40                  50
MVIMGQCYYNETIGFFYNNSGKELSSHWRPKDVVVVALGLTVSVLVLLTN 51                  60                  70                  80                  90                  100
LLVIAAIASNRRFHQPIYYLLGNLAAADLFAGVAYLFLMFHTGPRTARLS 101                 110                 120                 130                 140                 150
LEGWFLRQGLLDTSLTASVATLLAIAVERHRSVMAVQLHSRLPRGRVVML 151                 160                 170                 180                 190                 200
IVGVWVAALGLGLLPAHSWHCLCALDRCSRMAPLLSRSYLAVWALSSLLV 201                 210                 220                 230                 240                 250
FLLMVAVYTRIFFYVRRRVQRMAEHVSCHPRYRETTLSLVKTVVIILGAF 251                 260                 270                 280                 290                 300
VVCWTPGQVVLLLDGLGCESCNVLAVEKYFLLLAEANSLVNAAVYSCRDA 301                 310                 320                 330                 340                 350
EMRRTFRRLLCCACLRQSTRESVHYTSSAQGGASTRIMLPENGHPLMTPP 351                 360                 370                 380
FSYLELQRYAASNKSTAPDDLWVLLAQPNQQD
```

FIGURE 2: EDG4 NUCLEOTIDE SEQUENCE

```
   1  ggcacgaggc gccgggccat gggcctcgag cccgccccga accccgcga gcccgccttg
  61  tctgcggcgt gactggaggc ccagatggtc atcatgggcc agtgctacta caacgagacc
 121  atcggcttct tctataacaa cagtggcaaa gagctcagct cccactggcg gcccaaggat
 181  gtggtcgtgg tggcactggg gctgaccgtc agcgtgctgg tgctgctgac caatctgctg
 241  gtcatagcag ccatcgcctc caaccgcctc ttccaccagc ccatctacta cctgctcggc
 301  aatctggccg cggctgacct cttcgcgggc gtggcctacc tcttcctcat gttccacact
 361  ggtccccgca cagcccgact ttcacttgag ggctggttcc tgcggcaggg cttgctggac
 421  acaagcctca ctgcgtcggt ggccacactg ctggccatcg ccgtggagcg gcaccgcagt
 481  gtgatggccg tgcagctgca cagccgcctg ccccgtggcc gcgtggtcat gctcattgtg
 541  ggcgtgtggg tggctgccct gggcctgggg ctgctgcctg cccactcctg gcactgcctc
 601  tgtgccctgg accgctgctc acgcatggca ccctgctca gccgctccta tttggccgtc
 661  tgggctctgt cgagcctgct tgtcttcctg ctcatggtgg ctgtgtacac ccgcattttc
 721  ttctacgtgc ggcggcgagt gcagcgcatg gcagagcatg tcagctgcca cccccgctac
 781  cgagagacca cgctcagcct ggtcaagact gttgtcatca tcctggggc gttcgtggtc
 841  tgctggacac caggccaggt ggtactgctc ctggatggtt taggctgtga gtcctgcaat
 901  gtcctggctg tagaaaagta cttcctactg ttggccgagg ccaactcact ggtcaatgct
 961  gctgtgtact cttgccgaga tgctgagatg cgccgcacct tccgccgcct tctctgctgc
1021  gcgtgcctcc gccagtccac ccgcgagtct gtccactata catcctctgc ccagggaggt
1081  gccagcactc gcatcatgct tcccgaacca ggccacccac tgatgactcc acctttagc
1141  taccttgaac ttcagcggta cgcggcaagc aacaaatcca cagccctga tgacttgtgg
1201  gtgctcctgg ctcaacccaa ccaacaggac tgactgactg gcaggacaag gtctggcatg
1261  gcacagcacc actgccaggc ctcccaggc acaccactct gcccagggaa tgggggcttt
1321  gggtcatctc ccactgcctg ggggagtcag atggggtgca ggaatctgca tcttcagcca
1381  tctcaggttt agggggtttg taacagacat tattctgttt tcactgcgta tccttggtaa
1441  gccctgtgga ctggttcctg ctgtgtgatg ctgagggttt taaggtgggg agagataagg
1501  gctctctcgg gccatgctac ccggtatgac tgggtaatga ggacagactg tggacacccc
1561  atctacctga gtctgattct ttagcagcag agactgaggg gtgcagagtg tgagctggga
1621  aaggtttgtg gctccttgca gcctccaggg actggcctgt ccccaataga attgaagcag
1681  tccacgggga ggggatgata caaggagtaa acctttcttt acactcaaaa aaaa
```

FIGURE 3: EDG5 AMINO ACID SEQUENCE

```
  1         10         20         30         40         50
  |         |          |          |          |          |
MGSLYSEYLNPNKVQEHYNYTKETLETQETTSRQVASAFIVILCCAIVVE 51         60         70         80         90        100
  |         |          |          |          |          |
NLLVLIAVARNSKFHSAMYLFLGNLAASDLLAGVAFVANTLLSGSVTLRL 101        110        120        130        140        150
  |         |          |          |          |          |
TPVQWFAREGSASITLSASVFSLLAIAIERHVAIAKVKLYGSDKSCRMLL 151        160        170        180        190        200
  |         |          |          |          |          |
LIGASWLISLVLGGLPILGWNCLGHLEACSTVLPLYAKHYVLCVVTIFSI 201        210        220        230        240        250
  |         |          |          |          |          |
ILLAIVALYVRIYCVVRSSHADMAAPQTLALLKTVTIVLGVFIVCWLPAF 251        260        270        280        290        300
  |         |          |          |          |          |
SILLLDYACPVHSCPILYKAHYFFAVSTLNSLLNPVIYTWRSRDLRREVL 301        310        320        330        340        350
  |         |          |          |          |          |
RPLQCWRPGVGVQGRRRVGTPGHHLLPLRSSSSLERGMHMPTSPTFLEGN

351
  |
TVV
```

FIGURE 4: EDG5 NUCLEOTIDE SEQUENCE

```
   1 atgggcagct tgtactcgga gtacctgaac cccaacaagg tccaggaaca ctataattat
  61 accaaggaga cgctggaaac gcaggagacg acctcccgcc aggtggcctc ggccttcatc
 121 gtcatcctct gttgcgccat tgtggtggaa aaccttctgg tgctcattgc ggtggcccga
 181 aacagcaagt tccactcggc aatgtacctg tttctgggca acctggccgc ctccgatcta
 241 ctggcaggcg tggccttcgt agccaatacc ttgctctctg gctctgtcac gctgaggctg
 301 acgcctgtgc agtggtttgc ccgggagggc tctgcctcca tcacgctctc ggcctctgtc
 361 ttcagcctcc tggccatcgc cattgagcgc cacgtggcca ttgccaaggt caagctgtat
 421 ggcagcgaca agagctgccg catgcttctg ctcatcgggg cctcgtggct catctcgctg
 481 gtcctcggtg gcctgcccat ccttggctgg aactgcctgg gccacctcga ggcctgctcc
 541 actgtcctgc ctctctacgc caagcattat gtgctgtgcg tggtgaccat cttctccatc
 601 atcctgttgg ccatcgtggc cctgtacgtg cgcatctact gcgtggtccg ctcaagccac
 661 gctgacatgg ccgccccgca gacgctagcc ctgctcaaga cggtcaccat cgtgctaggc
 721 gtctttatcg tctgctggct gcccgccttc agcatcctcc ttctggacta tgcctgtccc
 781 gtccactcct gcccgatcct ctacaaagcc cactactttt tcgccgtctc caccctgaat
 841 tccctgctca acccgtcat ctacacgtgg cgcagccggg acctgcggcg ggaggtgctt
 901 cggccgctgc agtgctggcg ccgggggtg ggggtgcaag gacggaggcg ggtcgggacc
 961 cggggccacc acctcctgcc actccgcagc tccagctccc tggagagggg catgcacatg
1021 ccacgtcac ccacgtttct ggagggcaac acggtggtct_ga
```

FIGURE 5: EST No. AA419064

```
GGGCCATGGCTCGAGCCGCCCCGACCCCCCGCGAGCCCGCCTTGTCTGCGGCGTGACTGG
AGGCCCAGATGGTCATCATGGGCCAGTGCTACTACAACGAGACCATCGGCTTCTTCTATA
ACAACAGTGGCAAAGAGCTCAGCTCCCACTGGCGGCCCAAGGATGTGGTCGTGGTGGCAC
TGGGGCTGACCGTCAGCGTGCTGGTGCTGCTGACCAATCTGCTGGTCATAGCAGCCATCG
CCTCCAACCGCCGCTTCCACCAGCCCATCTACTACCTGCTCGGCAATCTGGCCGCGGCTG
ACCTCTTCGCGGGCGTGGCTACCTCTTCCTCATGTTCCACACTGGTCCCCGCACAGCCCG
ACTTTCACTTGAGGG
```

HUMAN POLYPEPTIDE RECEPTORS FOR LYSOPHOSPHOLIPIDS AND SPHINGOLIPIDS AND NUCLEIC ACIDS ENCODING THE SAME

This invention was made with government support under Grant No. HL31809, awarded by the National Institutes of Health. The Government has certain rights in this invention.

FIELD OF THE INVENTION

The invention relates to novel human membrane protein receptors for iysophospholipids and sphingolipids, and nucleic acids encoding these receptors. The invention is also directed to the use of these receptors in the discovery of agents that mediate or modulate apoptosis, cell proliferation, and other biological pathways in which phospholipid mediators are implicated.

BACKGROUND OF THE INVENTION

Lysophosphatidic acid (LPA) and sphingosine 1-phosphate (S1P) are potent phospholipid mediators with diverse biological activities. Their appearance and functional properties suggest possible roles in development, wound healing, and tissue regeneration. LPA and S1P appear to act in different cellular systems as paracrine, autocrine, and perhaps intracellular messengers. LPA and S1P are generated by complex enzymatic pathways from membranes of many different types of stimulated cells (Moolenar, W. H., *J. Biol. Chem* 270:12949 (1995); Spiegel and Milstein, *J. Membrane Biol.* 146:225 (1995); and Brindley et al., *Biochem. Cell. Biol.* 74:469 (1996)). LPA and S1P are both characterized by widespread cellular production, micromolar maximal concentrations in serum and some tissue fluids, high levels of binding to serun albumin and biodegradation by multiple enzymatic mechanisms (Fourcade et al., *Cell* 80:919 (1995); and Wang et al., *J. Biol. Chem.* 272:22030 (1997)). In extracellular fluids, these lipids are potent stimuli of cellular proliferation, differentiation, survival, adhesion, aggregation and other specific functions (Moolenaar et al., *Curr. Opin. Cell Biol.* 9:168 (1997; Gomez-Munoz et al., *J. Biol. Chem.* 210:26318 (1995); and Wu et al., *J. Biol. Chem* 270:11484 (1995)). LPA and S1P stimulate cellular proliferation directly by eliciting the serum response factor (SRF) and ternary complex factor (TCF) transcription factors, which together bind to and activate the serum response element (SRE) in promoters of many immediate-early genes (Hill, C. S. & Treisman, R., *EMBO J.* 14:5037–5042 (1995)).

The capacities of LPA and S1P to enhance cellular survival recently have been attributed in part to suppression of apoptosis (Cuvillier et al., *J. Biol .Chem.* 273:2910 (1998); Geotzl et al., *J. Immunol.* 162:2049 (1999); and Levine et al., *Am. J. Physiol.* 273:F575 (1997)). However, the complex mechanisms by which these lipids suppress apoptosis have not been elucidated fully. The specificity of LPA and S1P binding and initiation of signal transduction in numerous mammalian cells suggested that the actions of LPA and S1P are mediated by specific cell surface receptors (Van der Bend et al., *EMBO J.* 11:2495–2501 (1992)). The existence of G protein-coupled receptors (GPCRs) for LPA and S1P was suggested initially by specific ligand structural-dependence of their effects, ligand-induced desensitization of some cellular responses, and pertussis toxin inhibition of their cellular $Ca^{++}$ mobilizing and proliferative activities (Durieux and Lynch, *Trends Pharmac. Sci* 14:249 (1993); and Goodemote et al., *J. Biol. chem.* 270:10272 (1995).

Various GPCRs for LPA and S1P, have been identified (Hecht et al., *J. Cell Biol.* 135:1071 (1996); An et al., *Biochem. Biophys. Res. Commun.* 231:619–622 (1997); and Guo et al., *Proc. Natl. Acad. Sci. USA* 93:1436–1432 (1996).

The identification of additional LPA and S1P receptors is of interest because new receptors could provide additional tools for defmiing the mechanisms of LPA and S1P signaling and their physiological functions, and for identifying bioactive agents that simulate, modulate or mediate the functions of LPA and S1P.

SUMMARY OF THE INVENTION

In one of its several aspects, the invention provides isolated native sequences of the human Edg4 and Edg5 proteins, comprising the amino acid sequence of FIG. 1 (SEQ ID NO: 1) and FIG. 3 (SEQ ID NO:3), respectively.

In another aspect, the invention concerns an isolated Edg4 or Edg5 polypeptide, comprising an amino acid sequence having at least 85% sequence identity, preferably at least about 90% sequence identity, and most preferably at least about 95% sequence identity to the sequence of FIG. 1 (SEQ ID NO:1), or FIG. 3 (SEQ ID NO:3).

The invention also provides nucleic acids that encode the above-mentioned Edg4 and Edg5 polypeptides, as well as expression vectors and host cells comprising the Edg4- and Edg5-encoding nucleic acids. In one aspect, the isolated nucleic acid comprises DNA having at least 85% sequence identity, preferably at least about 90% sequence identity, most preferably at least about 95% sequence identity to a DNA molecule selected from the group consisting of (a) a DNA molecule encoding an Edg4 polypeptide having the sequence of FIG. 1 (SEQ ID NO: 1), (b) the complement of the DNA molecule of (a), (c) a DNA molecule encoding an Edg5 polypeptide having the sequence of FIG. 3 (SEQ ID NO:3), and (d) the complement of the DNA molecule of (c).

In another aspect, the isolated nucleic acid molecule encodes an Edg4 or Edg5 polypeptide and comprises DNA that hybridizes, preferably under stringent hybridization and wash conditions, to the complement of nucleic acid residues 85 through 1230 of FIG. 2 (SEQ ID NO:2), or to the complement of nucleic acid residues 1 through 1059 of FIG. 4 (SEQ ID NO:4).

In a still further aspect, the invention concerns an isolated nucleic acid molecule comprising DNA encoding a polypeptide having at least 85% sequence identity, more preferably at least about 90% sequence identity, most preferably at least about 95% sequence identity to either the amino acid sequence of FIG. 1 (SEQ ID NO:1) or FIG. 3 (SEQ ID NO:3), or the complement of such DNA.

The inventiion further provides screening assays for detecting the ability of a bioactive agent to simulate or modulate the activity of a lysophospholipid or sphingolipid for which the Edg4 or Edg5 polypeptide is a receptor. In the screening assay, a host cell comprising recombinant nucleic acid encoding an Edg4 or Edg5 polypeptide, and therefore expressing an Edg4 or Edg5 receptor, is contacted with a candidate bioactive agent, and the effects of the candidate bioactive agent directly on the cells and on lysophospholipid or sphingolipid cellular activities is determiined.

The invention additionally provides screening assays for detecting the ability of a bioactive agent to modulate the expression or activity of an Edg4 or Edg5 protein in a host cell, wherein a host cell comprising recombinant nucleic acid encoding an Edg4 or Edg5 polypeptide is contacted with a candidate bioactive agent, and the effects of the candidate bioactive agent on Edg4 or Edg5 expression or activity is determined.

In yet another embodiment, the invention concerns agonists and antagonists of a native Edg4 and/or Edg5 polypeptide. In a particular embodiment, the agonist or antagonist is an anti-Edg4 or anti-Edg5 antibody. In a further embodiment, the invention concerns a method of identifying agonists or antagonists of a native Edg4 and/or Edg5 polypeptide, by contacting the native Edg polypeptide with a candidate molecule and monitoring a biological activity mediated by said polypeptide, such as the binding of the polypeptide with its correlative ligand. In a still further embodiment, the invention concerns a composition comprising an Edg 4 and/or Edg5 polypeptide, or an agonist or antagonist as hereinabove defined, in combination with a pharmaceutically acceptable carrier.

BRIEF DESCRIPTION OF THE DRAWMNGS

FIG. 1 shows the derived amino acid sequence (SEQ ID NO: 1) of the human Edg4 polypeptide.

FIG. 2 shows the nucleotide sequence (SEQ ID NO:2) of a cDNA encoding the human Edg4 polypeptide. The start codon at nucleotides 85–87 and the stop codon at nucleotides 1231–1233, are underlined.

FIG. 3 shows the derived amino acid sequence (SEQ ID NO:3) of the human Edg5 polypeptide.

FIG. 4 shows the nucleotide sequence (SEQ ID NO:4) of a cDNA encoding the human Edg5 polypeptide. The start codon at nucleotides 1–3 and the stop codon at nucleotides 1060–1, are underlined.

FIG. 5 shows the nucleotide sequence (SEQ ID NO:5) of an expressed sequence tag (EST) used in the methods described herein.

DETAILED DESCRIPTION OF THE PREFERRED EMBODIMENTS

In one aspect, the terms Edg4 and Edg5 "polypeptide" or "protein" encompass native amino acid sequences of Edg4 and Edg5 and variants thereof. Native Edg4 and Edg5 polypeptides comprise the same amino acid sequence as Edg4 and Edg5 polypeptides isolated from mammalian tissue. Preferably, the native Edg4 or Edg5 polypeptide is isolated from human tissue. Isolated Edg4 or Edg5 polypeptides can also be prepared by recombinant and/or synthetic methods. Thus, as used herein, the term "isolated Edg4 or Edg5 polypeptide" encompasses Edg4 and Edg5 polypeptides that have been identified and recovered from a component of their normal environment, typically using one or more purification steps known in the art. The term also encompasses Edg4 and Edg5 polypeptides that are not within their normal environment, and thus includes Edg4 and Edg5 polypeptides expressed in situ within recombinant cells.

In one embodiment of the invention, the native Edg4 polypeptide sequence has the sequence of FIG. 1 (SEQ ID NO: 1), either with or without the signal sequence. In another embodiment of the invention, the native Edg5 sequence has the sequence of FIG. 3 (SEQ ID NO:3), either with or without the signal sequence.

As defined herein, Edg4 or Edg5 polypeptide variants exhibit Edg4 and Edg5 activity in that they act as GPCRs for LPA and S1P, respectively. The Edg4 or Edg5 polypeptide variants have at least 85% amino acid sequence identity with the amino acid sequence of FIG. 1 (SEQ ID NO: 1) or FIG. 3 (SEQ ID NO: 3), respectively, with or without the signal sequence. Edg4 and Edg5 polypeptide variants include, for instance, Edg 4 or Edg5 polypeptides wherein one or more amino acid residues are added, or deleted, at the N- or C-terminus, as well as within one or more internal domains, of the sequence of FIG. 1 (SEQ ID NO: 1) or FIG. 3 (SEQ ID NO: 3). Preferably, the Edg 4 or Edg 5 variant will have at least about 90% amino acid sequence identity, and more preferably at least about 95% sequence identity with the amino acid sequence of FIG. 1 (SEQ ID NO:1), or FIG. 3 (SEQ ID NO:3), respectively.

As used herein, the term "percent (%) amino acid sequence identity" means the value obtained using the BLASTP program of the BLAST 2.0 program family (using default parameters) described by Altschul etal., *Nucleic Acids Res.* (1997) 25:3389–3402.

Briefly, the program determines the percentage of amino acid residues in a candidate sequence that are identical with the amino acid residues in the sequence being compared (e.g. the sequence of FIG. 1 or the sequence of FIG. 3), after aligning the sequences and introducing gaps, if necessary, to achieve the maximum percent sequence identity, and not considering any conservative substitutions as part of the sequence identity. A % amino acid sequence identity value is determined by the number of matching identical residues divided by the total number of residues of the "longer" sequence in the aligned region. The "longer" sequence is the one having the most actual residues in the aligned region (gaps introduced by the program to maximize the alignment score are ignored).

The invention is also directed to isolated nucleic acid molecules that encode Edg4 and Edg5 polypeptides. An "isolated" nucleic acid molecule encoding an Edg4 or Edg5 polypeptide is a nucleic acid molecule that is identified and separated from at least one contaminant nucleic acid molecule with which it is ordinarily associated in the natural source of the Edg4- or Edg5-encoding nucleic acid. Thus, while an isolated Edg4- or Edg5-encoding nucleic acid molecule is distinguished from the Edg4- or Edg5-encoding nucleic acid molecule as it normally exists in natural cells, it includes expression vectors and host cells comprising the Edg4 and Edg5-encoding nucleic acids.

In one aspect, the isolated nucleic acid comprises DNA having at least 85% sequence identity, preferably at least about 90% sequence identity, most preferably at least about 95% sequence identity to a DNA molecule selected from the group consisting of (a) a DNA molecule encoding an Edg4 polypeptide having the sequence of FIG. 1 (SEQ ID NO: 1), (b) the complement of the DNA molecule of (a), (c) a DNA molecule encoding an Edg5 polypeptide having the sequence of FIG. 3 (SEQ ID NO:3), and (d) the complement of the DNA molecule of (c). The term "percent (%) nucleic acid sequence identity", as used herein, means the value obtained using the BLASTN program of the BLAST 2.0 program family described by Altschul et al., supra (using default paramaters, with overlap span and overlap fraction set to 1 and 0.125, respectively). Briefly, the percentage of nucleotide residues in a candidate sequence that are identical with the nucleotide residues in the sequence being compared. The sequence being compared may be the coding sequence of an Edg 4 polypeptide (e.g. nucleotides 85 through 1230 of FIG. 2 (SEQ ID NO:2), or an Edg5 polypeptide (the sequence of FIG. 4 (SEQ ID NO:4).

The isolated nucleic acid molecules of the present invention can also be defined in terms of their ability to hybridize to the Edg4 or Edg5 coding sequence set forth in FIG. 2 (SEQ ID NO:2) and FIG. 4 (SEQ ID NO:4), respectively. Preferably the isolated nucleic acid encoding Edg4 or Edg5 polypeptide comprises DNA that hybridizes under moderately stringent hybridization and wash conditions, and more preferably, under high stringency conditions, to the complement of nucleic acid residues 85 through 1230 of FIG. 2 (SEQ ID NO:2), or to the complement of nucleic acid residues 1 through 1059 of FIG. 4 (SEQ ID NO:4), respectively.

As used herein, "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash of 0.1×SSC containing EDTA at 55° C.

As used herein, "moderately stringent conditions' may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37–50° C.

Using the Edg4 and Edg5 polypeptides described herein, or antigenic fragments thereof, antibodies that specifically bind to Edg4 and Edg5 receptors can be prepared, such as the mouse monoclonal antibodies described in Goetzl et al., *J. Immunol*, (1999), supra. Preferably the anti-Edg4 and anti-Edg5 antibodies specifically bind Edg4 and Edg5 polypeptides, respectively, with a binding constant of at least $10^4$ $M^{-1}$, and preferably, in the range of $10^7$–$10^{-9}$ $M^{-1}$. The antibodies can be used for diagnostic purposes, to detect the presence of Edg4 and Edg5 proteins, using methods known in the art. Antibodies can also be used to signal cells through the Edg-4 and Edg-5 receptors, to block such signals, or eliminate the ability of Edg4 and Edg5 to bind to LPA and S1P, respectively.

The Edg4 and Edg5 polypeptides of the present invention can be used in screening assays designed to determine the effect of a candidate bioactive agent on (1) the expression and/or activity of Edg4 and/or Edg5 polypeptides, and/or (2) the function of LPA and/or S1P. The term "bioactive agent", as used herein, refers to any molecule or composition that can simulate, mediate or modulate the activity of LPA or S1P and/or Edg4 or Edg5 polypeptides. For example, the bioactive agent may partially or fully block the ability of an Edg4 or Edg5 receptor to bind to LPA or S1P. An example of such a bioactive agent includes an antibody that specifically binds to an extracellular domain of an Edg4 or Edg5 polypeptide. Another example is an antisense nucleic acid sequence that blocks transcription of an Edg4 or Edg5 gene, such as described in Goetzl et al., *J. Immunol*, (1999), supra. Bioactive agents may also enhance the activity of LPA and/or S1P, or the expression of Edg4 and/or Edg5 polypeptides.

In addition to the full-length native sequence Edg4 and Edg5 polypeptides described herein, it is contemplated that Edg4 and Edg5 variants can also be prepared. Edg4 and Edg5 variants can be prepared by introducing appropriate nucleotide changes into the Edg4 or Edg5 DNA, respectively, and/or by synthesis of the desired Edg4 or Edg5 polypeptide. Those skilled in the art will appreciate that amino acid changes may alter post-translational processes of the Edg4 and Edg5 polypeptides, such as changing the number or position of glycosylation sites or altering the membrane anchoring characteristics.

Variations in the native full-length sequence Edg4 and Edg5 polypeptides, or in various domains of the Edg4 or Edg5 polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the Edg4 or Edg5 polypeptide that results in a change in the amino acid sequence of the Edg4 or Edg5 polypeptide as compared with the native sequence Edg4 or Edg5 polypeptide. Optionally the variation is by substitution of at least one amino acid with any other amino acid in one or more of the domains of the Edg4 or Edg5 polypeptides. Guidance in determining which amino acid residue may be inserted, substituted or deleted without adversely affecting the desired activity may be found by comparing the sequence of the Edg4 or Edg5 polypeptide with that of homologous known protein molecules such as other Edg polypeptides and minimizing the number of amino acid sequence changes made in regions of high homology.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for the binding activity exhibited by the full-length or mature native sequence as described in Example 3.

The variations can be made using, methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the Edg4 or Edg5 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the betacarbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of variant, an isomeric amino acid can be used.

A. MODIFICATIONS OF EDG4 AND EDG5

Covalent modifications of Edg4 and/or Edg5 polypeptides are included within the scope of this invention. One type of covalent modification includes reacting targeted amino acid residues of a Edg4 or Edg5 polypeptide with an organic derivatizing agent that is capable of reacting with selected side chains or the N- or C-terminal residues of the Edg4 or Edg5 polypeptide. Derivatization with bifunctional agents is useful, for instance, for crosslinking Edg4 or Edg5 to a water-insoluble support matrix or surface for use in the method for purifying anti-Edg4 or Edg5 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: *Structure and Molecular Properties*, W. H. Freeman & Co., San Francisco, pp. 79–86 (1983)], acetylation of the N-terminal amine, and amidation of any C-terminal carboxyl group.

Another type of covalent modification of the Edg4 or Edg5 polypeptides included within the scope of this invention comprises altering the native glycosylation pattern of the polypeptide. "Altering the native glycosylation pattern" is intended for purposes herein to mean deleting one or more carbohydrate moieties found in native sequence Edg4 or Edg5 polypeptides (either by removing the underlying glycosylation site or by deleting the glycosylation by chemical and/or enzymatic means), and/or adding one or more glycosylation sites that are not present in the native sequence Edg4 or Edg5 polypeptides. In addition, the phrase includes qualitative changes in the glycosylation of the native proteins, involving a change in the nature and proportions of the various carbohydrate moieties present.

Addition of glycosylation sites to the Edg4 or Edg5 polypeptide may be accomplished by altering the amino acid sequence. The alteration may be made, for example, by the addition of, or substitution by, one or more serine or threonine residues to the native sequence Edg4 or Edg5 polypeptide (for O-linked glycosylation sites). The Edg4 or Edg5 amino acid sequence may optionally be altered through changes at the DNA level, particularly by mutating the DNA encoding the Edg4 or Edg5 polypeptide at preselected bases such that codons are generated that will translate into the desired amino acids.

Another means of increasing the number of carbohydrate moieties on the Edg4 or Edg5 polypeptide is by chemical or enzymatic coupling of glycosides to the polypeptide. Such methods are known to and described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the Edg4 or Edg5 polypeptide may be accomplished chemically or enzymatically or by mutational substitution of codons encoding for amino acid residues that serve as targets for glycosylation. Chemical deglycosylation techniques are known in the art and described, for instance, by Hakimuddin et al., *Arch. Biochem. Biophys.*, 259:52 (1987) and by Edge et al., *Anal,* *Biochem.*, 118:131 (1981). Enzymatic cleavage of carbohydrate moieties on polypeptides can be achieved by the use of a variety of endo- and exo-glycosidases as described by Thotakura et al., *Meth. Enzmmol.*, 138:350 (1987).

Another type of covalent modification of Edg4 and Edg5 polypeptides comprises linking the Edg4 and/or Edg5 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The Edg4 and Edg5 polypeptides of the present invention may also be modified in a way to form a chimeric molecule comprising either portions of or a whole Edg4 or Edg5 polypeptide fused to each other, or alternatively to another, heterologous polypeptide or amino acid sequence.

In one embodiment, such a chimeric molecule comprises a fusion of the Edg4 or Edg5 polypeptide with a tag polypeptide which provides an epitope to which an anti-tag antibody can selectively bind. The epitope tag is generally placed at the amino- or carboxyl-terminus of the Edg4 or Edg5 polypeptide. The presence of such epitope-tagged forms of the Edg4 and/or Edg5 can be detected using an antibody against the tag polypeptide. Also, provision of the epitope tag enables the solubilized Edg4 or Edg5 polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechlology*, 6:1204–1210 (1988)]; the KT3 epitope peptide [Martin et al., *Science*, 255:192–194 (1992)]; an α-tubulin epitope peptide [Skinner et al., *J. Biol, Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule may comprise a fusion of the Edg4 or Edg5 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a Edg4 and Edg5 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG-1 molecule. For the production of immunoglobulin fusions see also U.S. Pat. No. 5,428,130 issued Jun. 27, 1995.

The Edg4 and Edg5 polypeptides of the present invention may also be modified in a way to form a chimeric molecule comprising a Edg4 or Edg5 polypeptide fused to a leucine zipper. Various leucine zipper polypeptides have been described in the art. See, e.g., Landschulz et al., *Science* 240:1759 (1988); WO 94/10308; Hoppe et al., *FEBS Letters* 344:1991 (1994); Maniatis et al., *Nature* 341:24 (1989). It is believed that use of a leucine zipper fused to an Edg4 or Edg5 polypeptide may be desirable to assist in dimerizing or trimerizing soluble Edg4 and Edg5 polypeptides in solution. Those skilled in the art will appreciate that the leucine zipper may be fused at either the N- or C-terminal end of the Edg4 or Edg5 molecule.

B. PREPARATION OF EDG4 AND EDG5 POLYPEPTEIDES

The description below relates primarily to production of Edg4 and Edg5 polypeptides by culturing cells transformed or transfected with a vector containing Edg4 and Edg5 nucleic acid. It is, of course, contemplated that alternative methods, which are well known in the art, may be employed to prepare Edg4 and Edg5 polypeptides. For instance, the Edg4 and Edg5 sequences, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the Edg4 or Edg5 polypeptides may be chemically synthesized separately and combined using chemical or enzymatic methods to produce the full-length Edg4 or Edg5 polypeptide.

1. Isolation of DNA Encoding Edg4 and Edg5

DNA encoding Edg4 or Edg5 may be obtained from a cDNA library prepared from tissue believed to possess the Edg4 or Edg5 mRNA and to express it at a detectable level. Accordingly, human Edg4 or Edg5 DNA can be conveniently obtained from a cDNA library prepared from human tissue, such as described in the Examples. The Edg4 or Edg5-encoding gene may also be obtained from a genomic library or by oligonucleotide synthesis.

Libraries can be screened with probes (such as antibodies to the Edg4 or Edg5 polypeptide or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Edg4 or Edg5 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al, supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length length sequence can be determined through sequence alignment using computer software programs such as ALIGN, DNAstar, BLAST, BLAST2 and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures to detect precursors and processing intermediates of mRNA that may not have been reverse-transcribed into cDNA, as described in Sambrook et al., supra.

2. Selection and Transformation of Host Cells

Host cells are transfected or transformed with expression or cloning vectors described herein for Edg4 and Edg5 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al, supra.

Methods of transfection are known to the ordinarily skilled artisan, for example, $CaPO_4$, lipotransfection and electroporation. Depending on the host cell used, transformation is performed using standard techniques appropriate to such cells. The calcium treatment employing calcium chloride, as described in Sambrook et al, supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, liposomes or other lipids, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for Edg4 or Edg5-encoding vectors. *Saccharomyces cerevisiae* is a conmuonly used lower eukaryotic host microorganism.

Suitable host cells for the expression of glycosylated Edg4 and Edg5 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad, Sci. USA*, 77:4216 (1980)); mouse sertoli cells (TM4, Mather, *Biol Reprod.*, 23:243–251 (1980)); human lung cells (W138, ATCC CCL 75); human liver cells (Hep G2, HB 8065); and mouse mammary tumor (MMT 060562, ATCC CCL51).

Preferred host cells include human T lymphoblastoma cells (Tsup1, Xia et al., *J. Clin. Immunol.*, 16:21 (1996)), which have been used, for example, to investigate Edg4 and Edg5 mediation of LPA and S1P effects on apoptosis (see Goetzl et al., *J. Immunol*, (1999), supra) and also their mediation of LPA and S1P enhancement of T cell sensitivity to diptheria toxin (see Goetzl et al. (1999), *Proc. Assoc. American Phys.*, in press), as well as Jurkat leukemic T cells (An et al.,. *FEBS Letters* 417:279 (1997), as described in the Examples below. The selection of the appropriate host cell is deemed to be within the skill in the art.

3. Selection and Use of a Replicable Vector

The nucleic acid (e.g., cDNA or genomic DNA) encoding Edg4 or Edg5 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The Edg4 and Edg5 polypeptides may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the Edg4 or Edg5-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Expression and cloning vectors will typically contain a selection gene, also termed a selectable marker. Typical selection genes encode proteins that (a) confer resistance to antibiotics or other toxins, e.g., hygromycin (such as REP4 plasmid, InVitrogen, San Diego, Calif.), ampicillin, neomycin, methotrexate, or tetracycline, (b) complement auxotrophic defhygromyciniciencies, or (c) supply critical nutrients not available from complex media, e.g., the gene encoding D-alanine racemate for *Bacilli*.

An example of suitable selectable markers for mammalian cells are those that enable the identification of cells competent to take up the Edg4 or Edg5-encoding nucleic acid, such as DHFR or thymidine kinase. An appropriate host cell when wild-type DHFR is employed is the CHO cell line deficient in DHFR activity, prepared and propagated as described by Urlaub et al., *Proc, Natl. Acad, Sci. USA*, 77:4216 (1980). A suitable selection gene for use in yeast is the trp1 gene present in the yeast plasmid YRp7 [Stinchcomb et al., *Nature*, 2:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the Edg4 or Edg5-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natt. Acad, Sci, USA*, 80:21–25 (1983)]. Promoters for use in bacterial systems also will contain a Shine-Dalgarno (S.D.) sequence operably linked to the DNA encoding Edg4 or Edg5.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Edg4 and/or Edg5 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the Edg4 and Edg5 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the Edg4 or Edg5 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Edg4 and/or Edg5.

Still other methods, vectors, and host cells suitable for adaptation to the synthesis of Edg4 and Edg5 in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence Edg4 or Edg5 polypeptide or against a synthetic peptide based on the DNA sequences provided herein or against an exogenous sequence fuised to the Edg4 or Edg5 DNA and encoding a specific antibody epitope.

Semiquantitative radioactive analyses of Tsup-1 cell mRNA using a reverse transcription-polymerase chain reaction method are described in Example 6 infra, and are described in more detail in Goetzl et al., *J. Immunol.* (1999), supra, for determining expression of Edg receptor proteins including Edg4 and Edg5. Western blot analyses of Tsup-1 cell Edg receptors developed with mouse monoclonal anti-Edg3, -4 and -5 receptors antibodies are described in Example 9 infra, and are described in more detail in Goetzl et al, *Proc. Assoc. American Physicians* (1999), in press.

5. Purification of Polypeptide

Forms of Edg4 and Edg5 may be recovered from culture medium or from host cell lysates. If membrane-bound, it can be released from the membrane using a suitable detergent solution (e.g. Triton-X 100) or by enzymatic cleavage. Cells employed in expression of Edg4 and Edg5 can be disrupted by various physical or chemical means, such as freeze-thaw cycling, sonication, mechanical disruption, or cell lysing agents.

It may be desired to purify Edg4 and Edg5 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the Edg4 and Edg5 polpeptides. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular Edg4 or Edg5 polypeptide produced.

C. USES FOR EDG4 AND EDG5 POLYPEPTEDES

The Edg4 and Edg5 polypeptides can be used, for example, in assays to identify other proteins or molecules involved in their binding interaction with LPA and S1P, respectively, as well as in screening assays for the identification of agents that affect LPA and S1P activities. By such methods, inhibitors of the receptor/ligand binding interaction can be identified. Proteins involved in such binding interactions can also be used to screen for peptide or small molecule inhibitors or agonists of the binding interaction. Also, the receptor Edg4 and/or Edg5 can be used to isolate any correlative ligand(s).

Screening assays can also be designed to find lead compounds that mimic the biological activity of a native Edg4 or Edg5 receptor, or their respective ligands LPA and S1P. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleotide sequences (or their complement) encoding Edg4 and Edg5 have various applications in the art of molecular biology, including uses as hybridization probes, in chromosome and gene mapping and in the generation of anti-sense RNA and DNA. Edg4 and/or Edg5 nucleic acids will also be useful for the preparation of Edg4 and Edg5 polypeptides by the recombinant techniques described herein.

The full-length native sequence Edg4 and Edg5 genes, or portions thereof, may be used as hybridization probes for a cDNA library to isolate the full-length Edg4 and Edg5 genes, respectively, or to isolate still other genes (for instance, those encoding Edg4 and Edg5 from other species)

which have a desired sequence identity to the Edg4 or Edg5 coding sequence. Optionally, the length of the probes will be about 20 to about 50 bases. The hybridization probes may be derived from the nucleotide sequence or from genomic sequences including promoters, enhancer elements and introns of native sequence Edg4 or Edg5. By way of example, a screening method will comprise isolating the coding region of the Edg4 or Edg5 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the Edg4 and/or Edg5 gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of other related Edg4 and/or Edg5 coding sequences. Nucleotide sequences encoding an Edg4 or Edg5 polypeptide can also be used to construct hybridization probes for mapping the gene which encodes Edg4 or Edg5, and for the genetic analysis of individuals with genetic disorders involving LPA or S1P. The nucleotide sequences provided herein may be mapped to a chromosome and specific regions of a chromosome using known techniques, such as in situ hybridization, linkage analysis against known chromosomal markers, and hybridization screening with libraries. A region on human chromosome 19 p12 encompassing most of the human Edg4 gene with multiple exons and introns has been sequenced by the Human Genome Project (GeneBank accession number AC002306).

Nucleic acids which encode Edg4 or Edg5 or their modified forms can also be used to generate either transgenic animals or "knock out" animals which, in turn, are useful in investigating the physiological and pathological roles of LPA or S1P, respectively, and in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding Edg4 or Edg5 can be used to clone genomic DNA encoding Edg4 or Edg5 in accordance with established techniques and the genomic sequences used to generate transgenic animals that contain cells which express DNA encoding Edg4 and Edg5.

Methods for generating transgenic animals, particularly animals such as mice or rats, have become conventional in the art and are described, for example, in U.S. Pat. Nos. 4,736,866 and 4,870,009. Typically, particular cells would be targeted for Edg4 and/or Edg5 transgene incorporation with tissue-specific enhancers. Transgenic animals that include a copy of a transgene encoding Edg4 or Edg5 introduced into the germ line of the animal at an embryonic stage can be used to examine the effect of increased expression of DNA encoding Edg4 Edg5. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of Edg4 or Edg5 can be used to construct an Edg4 or Edg5 "knock out" animal which has a defective or altered gene encoding Edg4 or Edg5 as a result of homologous recombination between the endogenous gene encoding Edg4 or Edg5 and altered genomic DNA encoding Edg4 or Edg5 introduced into an embryonic cell of the animal. For example, cDNA encoding Edg4 or Edg5 can be used to clone genoric DNA encoding Edg4 or Edg$^5$ in accordance with established techniques. A portion of the genomic DNA encoding Edg4 or Edg5 can be deleted or replaced with another gene, such as a gene encoding a selectable marker which can be used to monitor integration.

Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the Edg4 and/or Edg5 polypeptides.

Nucleic acid encoding the Edg4 and/or Edg5 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143–4146 (1986)). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into manmalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]).

In some situations it is desirable to provide the nucleic acid source with an agent that selectively targets the host cells, such as an antibody specific for a cell surface membrane protein or the host cell, a ligand for a receptor on the host cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol, Chem*, 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

D. ANTI-EDG4 AND EDG5 ANTIBODIES

The present invention further provides anti-Edg4 and Edg5 antibodies. Exemplary antibodies include polyclonal, monoclonal, humanized, bispecific, and heteroconjugate antibodies.

1. Polyclonal Antibodies

The anti-Edg4 and -Edg5 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Edg4 or Edg5 polypeptides or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-Edg4 and Edg5 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the Edg4 or Edg5 polypeptides or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human no monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against Edg4 or Edg5. Preferably, the binding specificity of monoclonal antibodies produced by the hybridoma cells is determined by immunoprecipitation or by an in vitro binding assay, such as radioinmmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal, Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide.

Such a non-immunoglobuim polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-Edg4 and Edg5 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human iminunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmnann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 33:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and. Boerner et al., *J. Immunol.*, 147(1):86–95 (1991)]. Similarly, human antibodies can be made by introducing human immunoglobulin gene loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern Rev. Immunol.* 13 65–93 (1995).

4. Bispecific Antibodies

Bispecific antibodies are monoclonal, preferably human or humanized, antibodies that have binding specificities for at least two different antigens. In the present case, one of the binding specificities is for the Edg4 or Edg5 polypeptides, the other one is for any other antigen, and preferably for a cell-surface protein or receptor or receptor subunit.

Methods for making bispecific antibodies are known in the art. Traditionally, the recombinant production of bispecific antibodies is based on the co-expression of two inimunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for an example, Suresh et al., *Methods in Enzmmology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercapto butyrimidate and those disclosed, for example, in U.S. Pat. No. 4,676,980.

E. USES FOR ANTI-EDG4 AND EDG5 ANTIBODIES

The anti-Edg4 and Edg5 antibodies of the invention have various utilities. For example, anti-Edg4 and Edg5 antibodies may be used in diagnostic assays for Edg4 and Edg5, respectively, e.g., detecting their expression in specific cells, tissues, or serumn. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$ $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-Edg4 and Edg5 antibodies also are useful for the affinity purification of Edg4 and Edg5, respectively, from recombinant cell culture or natural sources. In this process, the antibodies against Edg4 and/or Edg5 are immobilized on a suitable support, such a Sephadex resin or filter paper, using methods well known in the art. The immobilized antibody then is contacted with a sample containing the Edg4 and/or Edg5 to be purified, and thereafter the support is washed with a suitable solvent that will remove substantially all the material in the sample except the Edg4 and/or Edg5, which is bound to the immobilized antibody. Finally, the support is washed with another suitable solvent that will release the Edg4 or Edg5 from the antibody.

F. SCREENING ASSAYS EMPLOYING Edg4 AND Edg5 RECEPTORS

The assays herein utilize the Edg4 and Edg5 polypeptides as defined herein. In one embodiment, portions of the Edg 4 and Edg 5 polypeptides are utilized. In addition, the assays described herein may utilize either isolated Edg4 or Edg 5 polypeptides or cells comprising the Edg 4 or Edg5 polypeptides.

Generally, in a preferred embodiment of the methods herein, the solubilized Edg4 and/or Edg5 proteins or the candidate bioactive agent are non-diffusably bound to an insoluble support having isolated sample receiving areas (e.g. a microtiter plate, an array, etc.). The insoluble supports may be made of any composition to which the proteins or cells can be bound, is readily separated from soluble material, and is otherwise compatible with the overall method of screening. The surface of such supports may be solid or porous and of any convenient shape.

Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the isolated or cell-associated Edg receptor target and is nondiffusable.

Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used.

In a preferred embodiment, the Edg4 and/or Edg5 polypeptide is bound to the support, and a candidate bioactive agent is added to the assay. Alternatively, the candidate agent is bound to the support and the polypeptide is added. Novel binding agents include specific antibodies, non-natural binding agents identified in screens of chemical libraries, phospholipid analogs, peptide analogs, etc. Of particular interest are screening assays for agents that are highly bioavailable and have a low toxicity for human cells. A wide variety of assays may be used for this purpose, including labeled in vitro protein-ligand direct binding assays, nuclear transcription reporter assays, immunoassays for protein binding, biocheincial and functional assays (quantification of changes in $Ca^{++}$ or protein phosphorylation, etc.) and the like.

The determination of the binding of the candidate bioactive agent to the Edg4 and/or Edg5 polypeptide may be done in a number of ways. In a preferred embodiment, the candidate bioactive agent is labelled, and binding determined directly. For example, this may be done by attaching all or a portion of the Edg4 and/or Edg5 protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly coupled to a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be conjugated with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. Edg4 and/or Edg5), such as an antibody, peptide, binding partner, ligand, etc. In a preferred embodiment, the competitor is LPA for Edg 4 and S1P for Edg 5. Under certain circumstances, there may be competitive binding as between the bioactive agent and the binding moiety, with the binding moiety displacing the bioactive agent. This assay can be used, for example, to determine candidate antagonistic agents which interfere with binding between the Edg receptor proteins and their respective phospholipid mediators.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess first reagent is generally removed or washed away, if detection is dependent on a second reagent. The second component is then added, and the presence or absence of the labeled component is quantified, to indicate binding.

In a preferred embodiment, the competitor is added first, followed by the candidate bioactive agent. Displacement of the competitor is an indication that the candidate bioactive agent is binding to the Edg4 or Edg5 protein and thus is capable of binding to, and potentially modulating, the activity of the receptor. In this embodiment, either component can be labeled. Thus, for example, if the competitor ill is labeled, the presence of label in the wash solution indicates displacement by the agent. Alternatively, if the candidate bioactive agent is labeled, the presence of the label on the support indicates displacement.

In alternative embodiments, the candidate bioactive agent is added first, with incubation and washing, followed by the competitor, or the bioactive agent and the competitor are added together so as to obtain a steady state or equilibrium. The absence of binding by the competitor may indicate that the bioactive agent is bound to the Edg receptor protein with a higher affinity. Thus, if the candidate bioactive agent is labeled, the presence of the label on the support, coupled with a lack of competitor binding, may indicate that the candidate agent is capable of binding to the Edg receptor protein.

In a preferred embodiment, the methods comprise differential screening to identify bioactive agents that are capable of modulating the level of expression or signaling activity of the Edg proteins. In this embodiment, the methods comprise combining an Edg receptor protein and a competitor in a first sample. A second sample comprises a candidate bioactive agent, an Edg protein and a competitor. The binding of the competitor is determined for both samples, and a change, or difference in binding between the two samples indicates the presence of an agent capable of binding to the Edg receptor protein and potentially modulating its activity. That is, if the binding of the competitor is different in the second sample relative to the first sample, the agent is capable of binding to the Edg receptor protein.

Alternatively, a preferred embodiment utilizes differential screening to identify drug candidates that bind to the native Edg receptor protein, but cannot bind to a modified Edg receptor protein. The structure of the Edg protein may be modeled, and used in rational drug design to synthesize agents that interact with that site. Drug candidates that affect Edg receptor bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Carrier and delivery proteins and other types of molecules are especially important in studies of LPA and S1P. Also reagents that otherwise improve the efficiency of the assay, such as protease inhibitors, nuclease inhibitors, anti-microbial agents, etc., may be used. The mixture of components may be added in any order that provides for the requisite binding.

The components provided herein for the assays provided herein may also be combined to form kits. The kits can be based on the use of the protein and/or the nucleic acid encoding the Edg receptor proteins. Assays regarding the use of nucleic acids are further described below.

Screening for agents that modulate the activity of the Edg receptor may also be done. In a preferred embodiment, methods for screening for a bioactive agent capable of modulating the activity of the Edg receptor comprise the steps of adding a candidate bioactive agent to a sample of Edg, as above, and determining an alteration in the biological activity of the Edg receptor. "Modulating the activity of Edg" includes an increase in activity, a decrease in activity, or a change in the type or kind of activity present. Thus, in this embodiment, the candidate agent should both bind to the Edg receptor or another cellular molecule that regulates one or more Edg receptors (although this may not be necessary), and alter its biological or biochemical activity as defined herein. The methods include both in vitro screening methods, as are generally outlined above, and in vivo screening of cells for alterations in the presence, distribution, activity or amount of the desired Edg receptor.

In a preferred embodiment, the invention provides methods for screening for bioactive agents capable of modulating the activity of an Edg receptor protein. The methods comprise adding a candidate bioactive agent, as defined above, to a cell comprising the desired Edg receptor proteins. Preferred cell types include almost any cell. The cells may further contain a recombinant nucleic acid that encodes one or more Edg receptors to enhance expression of the desired receptor proteins, as described in Example 2 below. In a preferred embodiment, a library of candidate agents are tested on a plurality of cells.

In some embodiments, the assays include exposing the cells to an apoptotic agent that will induce apoptosis, such as described in Example 7 below, to evaluate Edg receptor expression or activity and their mediation of LPA and S1P prevention of apoptosis. Suitable apoptotic agents are known in the art and include but are not limited to removal of growth and tryptic factors, additions of anti-Fas antibody as well as antibodies to other cell surface receptors such as anti-CD2, anti-CD3 and anti-CD28 and the like, C6 ceramide, and a variety of additional chemical and physical agents. Alternatively; the cells may be exposed to conditions that normally result in cellular proliferation, to determine changes in Edg expression or activity and the role of LPA and S1P in stimulating cellular proliferation, as described in Example 9 below. Thus, the effect of the candidate agent on apoptosis or cellular proliferation is then evaluated.

In this way, bioactive agents are identified. Compounds with pharmacological activity are able to enhance or interfere with the activity of one or more of the Edg receptor proteins, or that simulate their respective ligands. The compounds having the desired pharmacological activity may be administered in a physiologically acceptable carrier to a host, as previously described, to maximize bioavailability. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the Edg receptor proteins are important in the signaling pathways for the phospholipid mediators LPA and S1P, which may play a role in development, wound healing, angiogenesis, cytoprotection, remyelination or neurons, tissue regeneration, and malignant transformation of cells. Accordingly, disorders based on mutant or variant Edg4 or Edg-5 genes may be determined. In one embodiment, the invention provides methods for identifying cells containing variant Edg genes comprising determining all or part of the sequence of at least one endogenous Edg gene in a cell. As will be appreciated by those in the art, this may be done using any number of sequencing techniques. In a preferred embodiment, the invention provides methods of identifying the Edg-4 and/or Edg-5 genotype of an individual comprising determining all or part of the sequence of at least one Edg gene of the individual. This is generally done in at least one tissue of the individual, and may include the evaluation of a number of tissues or different samples of the same tissue. The method may include comparing the sequence of the Edg gene to a known Edg gene, i.e. a wild-type gene.

The sequence of all or part of the Edg gene can then be compared to the sequence of a known Edg gene to determine if any differences exist. This can be done using any number of known sequence identity programs, such as Bestfit, etc. and others outlined herein. In a preferred embodiment, the presence of a difference in the sequence between the Edg gene of the patient and the known Edg gene is indicative of a disease state or a propensity for a disease state, as outlined herein.

In a preferred embodiment, the Edg proteins, and particularly Edg fragments, are useful in the study or treatment of conditions related to the phospholipid mediators LPA and S1P. This includes prevention of apoptosis and other potent cytoprotective effects of LPA and S1P in cardiac myocytes and neurons, induction of proliferation of endothelial cells in angiogenesis, repair of nerves by stimulation of oligodendrocytes, and promotion of growth and spread of many types of malignant tumors, especially breast, ovarian and prostate cancers. Thus, "disease state" includes conditions involving myocardial infarction, traumatic injury, inflammatory demyelination, neurodegeneration and cancer. In the first four states, LPA and S1P agonists are preferred agents and, in cancer, antagonists would be the preferred therapeutic agents.

The term "antagonist" is used in the broadest sense, and includes any molecule that partially or fully blocks, inhibits, or neutralizes a biological activity of a native Edg4 or Edg5 polypeptide disclosed herein. In a similar manner, the term "agonist" is used in the broadest sense and includes any molecule that mimics a biological activity of a native Edg4 or Edg5 polypeptide disclosed herein. Suitable agonist or antagonist molecules specifically include agonist or antagonist antibodies or antibody fragments, fragments or amino acid sequence variants of native Edg4 and Edg5 polypeptides, peptides, small organic molecules, etc.

Thus, in one embodiment, methods of modulating LPA and S1P activity in cells or organisms are provided. In one embodiment, the methods comprise administering to a cell an anti-Edg antibody or other agent identified herein or by the methods provided herein, that alters or eliminates the biological activity of the endogenous Edg-4 and/or Edg-5 receptor protein, or simulates the activity of its respective phopholipid ligand. Alternatively, the methods comprise administering to a cell or organism a recombinant nucleic acid encoding an Edg-4 and/or Edg-5 protein or modulator including anti-sense nucleic acids. As will be appreciated by those in the art, this may be accomplished in any number of ways. In a preferred embodiment, the Edg receptor activity is increased by increasing the amount of Edg protein in the cell, for example by overexpressing the endogenous Edg or by administering a gene encoding Edg-4 and/or Edg5, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entireity.

In one embodiment, the invention provides methods for diagnosing a LPA- or S1P-mediated condition in an individual. The methods comprise measuring the activity or expression of an Edg receptor protein in a tissue from the individual or patient. This is compared to the expression or activity of the Edg receptor protein from either an unaffected second individual or from an unaffected tissue from the first individual. When these activities are different, the first individual may be at risk for an LPA- or S1P-mediated disorder.

The proteins and nucleic acids provided herein can also be used for screening purposes wherein the protein-protein interactions of the Edg receptor proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., Proc Natl. Acad. Sci USA 88:10686 (1991); Fearon et al., Proc, Natl. Acad. Sci, USA 89:7958 (1992); Dang et al., Mol. Cell, Biol, 11:954 (1991); Chien et al., Proc. Natl. Acad. Sci. USA 88:9578 (1991); and U.S. Pat. Nos. 5,283,173, 5,667,973, 5,468,614, 5,525,490, and 5,637,463.

In general, two nucleic acids are transformed into a cell, where one is a "bait" such as the gene encoding BAIT or a portion thereof, and the other encodes a test candidate. Only if the two expression products bind to one another will an indicator, such as a fluorescent protein, be expressed. Expression of the indicator indicates when a test candidate binds to the bait and can be identified as an Edg protein. Using the same system and the identified Edg proteins the reverse can be performed. Namely, the Edg proteins provided herein can be used to identify new baits, or agents which interact with Edg proteins. Additionally, the two-hybrid system can be used wherein a test candidate is added in addition to the bait and the Edg protein encoding nucleic acids to determine agents which interfere with the bait, such as BAIT, and the Edg protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state such as those described above could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, cellular and chemical stimuli, etc., that may contribute to conditions which can effect protein—protein interactions.

Assays involving binding such as the two-hybrid system may take into account non-specific binding proteins (NSB). LPA and S1P are amphiphiles that show high levels of NSB in all assays, for which the only presently-available remedy is carrier-delivery proteins, such as fatty acid-free serum albumins or gelsolin.

The following examples are offered for illustrative purposes only, and are not intended to limit the scope of the present invention in any way. Commercially available reagents referred to in the examples were used according to manufacturer's instructions unless otherwise indicated.

EXAMPLES

Example 1

Isolation and Characterization of Edg4

The BLASTN program, described by Altschul et al., supra, was used to search the dbEST division of the public expressed sequence tag (EST) database, GenBank, to identify sequences homologous to that of human Edg2, which had been previously identified as a function receptor for LPA (An et al., (1997) *Biochem. Biophys, Res, Commun* 231:619–622. EST No. AA419064 (FIG. 5; SEQ ID NO:5), was identified as having significant, but not identical homology, to the 5' region of Edg2 cDNA clone (GenBank accession number 755526). The cDNA clone (GenBank accession number 755526) was obtained from I.M.A.G.E. Consortium through Genome Systems (St. Louis, Mo.). The entire 1.7 kb insert was sequenced on both strands using an ABI automated DNA sequencer (Howard Hughes Medical Institute DNA core facility, University of California, San Francisco).

The nucleotide sequence of cDNA clone 755526 was found to be highly homologous to that of human Edg2, and was therefore designated human Edg4. The novel polypeptide encoded thereby, which was designated Edg4 (FIG. 1; SEQ ID NO: 1) was found to be 46% identical and 72% similar to the human Edg2 LPA receptor. The Edg4 protein consists of 382 amino acids with an estimated molecular weight of 42,626 daltons. It has some of the common features of a GPCR, including seven putative transmembrane domains at about amino acids 34–57, 70–90, 109–128, 149–168, 192–209, 243–262, and 279–297 (indicated by underlining in FIG. 1); potential N-linked glycosylation sites at the N-terminus, and phosphorylation sites for serine/threonine kinases in each of the intracellular regions. Edg4 also possesses unique characteristics distinct from most other GPCRs. In Edg4, an alanine replaces a proline that is usually conserved in the NPXX Y sequence of the seventh transmembrane domain. As in Edg2, the first extracellular loop of Edg4 lacks a cystein residue that may form a disulfide bond with another cystein in the second extracellular loop in most other GPCRs.

The Edg4 protein is also related to several "orphan" GPCRs, with 34% amino acid sequence identity to rat H218 (MacLennan et al. (1994) *Mol. Cell. Neurosci.* 5:201–209), and 30% amino acid sequence identity to human Edg3 (GenBank accession number X83864). The human gene locus of Edg4 was sequenced and located on chromosome 19 p12 (GenBank accession number AC002306).

Example 2

Edg4 Reporter Gene Assay

The 1.7-kb insert of cDNA clone (GenBank accession number 755526) encoding Edg4 was cut out by Eco RI and Not I and subcloned into the mamnmalian expression vector pCDEF3 (Goldman et al.(1996) *BioTechniques* 21:1013–105), to result in an expression construct designated "Edg4/EF3". Similarly, the 1.1-kb cDNA coding region of human Edg2 was cleaved from Edg2/RSV (An et al., supra) and also subcloned into pCDEF3; the expression construct was designated "Edg2/EF3".

Jurkat leukemic T cells (obtained from Dr. Arthur Weiss, UCSF) were co-transfected with the SRE-luciferase reporter plasmid (An et al., supra) at a 1:10 ratio in combination with either Edg4/EF3, Edg2/EF3, or empty pCDEF3 vector using DMRIE-C lipofection reagent (Life Technologies, Inc.). After 4 hours of transfection incubation in OPTI-MEM medium (Life Technologies, Inc.) containing 10% fetal bovine serum, cells were washed and starved in serum-free RPMI 1640 at 37° C. for 8 hours. Cells were then washed and resuspended in serum-free RPMI 1640, and aliquots of $1 \times 10^5$ cells were transferred into 96-well plates. LPA and other phospholipids dissolved in serum-free RPMI 1640 containing 0.1 mg/ml of human serum albumin were added to the cells followed by a 10-h incubation at 37° C. Cells were then lysed by Reporter Lysis Buffer (Promega), and luciferase activities were measured using a Turner Designs 20/20 luminometer. To assess a G protein requirement, some aliquots of cells were incubated in the presence of 50 ng/ml of pertussis toxin (PTX) (Calbiochem, La Jolla, Calif.), 10 µg/ml of recombinant *Clostridium botulinum* C3 AD-ribotransferase (C3 exoenzyme), which specifically ADP-ribosylates Rho (Kumagai et al., *J. Biol. Chem.* 268:24535–24538), or both toxins during serum starvation and LPA treatment.

When co-transfected with SRE-luciferase reporter gene, Edg4, as Edg2, mediated increases in SRE-driven reporter gene expression induced by 1 µM LPA and, to a lesser extent, phosphatidic acid (PA). The activation of LPA-induced SRE-driven reporter gene in Edg4- and Edg2- transfected Jurkat cells was significant at 1 nM LPA, reached a maximum at 100 nM LPA, and exhibited an $EC_{50}$ of approximately 10 nM. PA mimics the effect of LPA in both Edg4- and Edg2-transfected Jurkat cells but with much higher $EC_{50}$ values of at least 500 nM. These results demonstrate that the PA-induced activation of SRE-driven reporter gene was dependent on Edg2 and Edg4 transfection. The higher $EC_{50}$ value of PA suggests that PA, if it acts directly on Edg2 and Edg4 receptors, is a much weaker agonist for these receptors. The magnitude of LPA- and PA-evoked SRE-driven reporter activation of Edg4 was approximately four times higher than that of Edg2. The structurally related lipids lysophosphatidyl-choline, lysophosphatidyl-ethanolamine, lysophosphatidyl-serine, and sphingosine 1-phosphate at a concentration of 1 μM failed to generate significant increases in luciferase expression. The control Jurkat cells transfected with empty pCDEF3 vector showed minimal changes in response to LPA or other phospholipids.

LPA-induced activation of the SRE reporter gene in both Edg2- and Edg4-transfected Jurkat cells was partially blocked by PTX or C3 exoenzyme pretreatment. The two toxins added together further inhibited the effects of LPA, suggesting that both the α subunit of $G_i$ and Rho GTPase are involved in transducing signals from the Edg2 and Edg4 receptors to the SRE reporter gene activation.

The present invention also contemplates other advantageous reporter gene constructs, including, for example, reporter gene assays using a CRE-luciferase construct (cAMP response element) as well as a NFAT-luciferase construct (nuclear factor AT response element).

Example 3

Edg4 Receptor Binding Assay

Jurkat T cells ($2\times10^7$ in OPTI-MEM) were transfected with 2 μg of Edg4/EF3 or empty pCDEF3 vector for 4 hours at 37° C. using Lipofectin (Life Technologies, Inc). The transfected cells were maintained in RPMI 1640 medium containing 10% fetal bovine serum for 12 hours at 37° C. and washed three times with phosphate-buffered saline (PBS) before assessment of binding. Duplicate 0.2-ml aliquots of $2\times10^6$ cells were incubated with 200,000 cpm of [$^3$H] LPA in 0.25% bovine serum albumnin-phosphate-buffered saline binding buffer for 45 minutes at 0° C. The final concentration of [$^3$H]LPA in the binding incubations was 10 nM. The binding cell suspensions were passed through GFIC filters that were washed with 12 ml of ice-cold PBS containing 0.05% Tween-20, air-dried, and added to scintillation fluid for quantification of radioactivity bound to the cells. Total and nonspecific binding were evaluated in the absence and the presence of 10 μM nonradioactive LPA, respectively. Specific binding was calculated from the difference in cpm between total binding and nonspecific binding.

The background-specific [$^3$H]LPA binding in the control vector-transfected Jurkat cells was 1409±123 cpm (mean±S.E., n=3), using fatty acid-free bovine serum albumin as the carrier protein. In the same number of Edg4-transfected Jurkat cells, the specific binding was 3082±298 cpm (mean±S.E. n=3), which was significantly higher than the controls (p<0.01). When calculated in terms of receptor density, control Jurkat cells had 15,000±1300 LPA-binding sites and Edg4 transfectants had 33,000±3200 binding sites. Thus, Edg4 overexpression in Jurkat cells resulted in increases in the number of specific binding sites for LPA.

Example 4

Edg4 Northern Blot Analysis

The 1.7-kb and 1.1-kb inserts of Edg4/EF3 and Edg2/EF3, respectively (described in Example 2) were labeled with $^{32}$P and used as probes in Northern blot analyses. Northern blots containing 2 μg of poly (A)$^+$ RNA from various human tissues and cancer cells in each lane were hybridized and washed under high stringency conditions Sambrook et al., supra. Blots were exposed to Kodak XAR film for 24 hours at −70° C. with one intensifying screen.

The Edg2 transcripts were found in almost all human tissues with the highest abundance in brain and the lowest abundance liver and peripheral blood leukocytes. The Edg2 transcripts were also detected in HeLa carcinoma, SW480 colorectal adenocarcinoma, A549 lung carcinoma, and G361 melanoma but were undetectable in HL60 promyelocytic leukemia, K562 chronic myelogenous leukemia, MOLT-4 lymphoblastic leukemia, and Raji Burkitt's lymphoma cells. In contrast, the two major Edg4 transcripts of 8 and 1.8 kb were not represented in human tissues as widely as Edg2 transcripts and showed a pattern of distribution completely different from Edg2. The 8-kb transcript was detected in peripheral blood leukocytes, thymus, and spleen, whereas the 1.8-kb transcript was in the leukocytes, testis, prostate, and pancrease. The Edg4 transcripts were almost undetectable in brain, heart, placenta, and digestive tract where Edg2 transcripts were abundant, but were found in leukocytes were Edg2 was undetectable. In cancer cells, the 8-kb transcript of Edg4 was found in all cell types, wheras the 1.8-kb transcript was only detected in HeLa, SW480, and A549 cells where Edg2 transcripts were also more abundant. In addition, a minor transcript of 2.8 kb was seen in G361 and SW480 cells. Detailed data is shown in An et al., *J. Biol. Chem.*, (1998) 273(14):7906–7910, incorporated herein by reference. The existence and distinctive tissue expression of structurally different LPA receptors, as demonstrated by these experiments, may provide one basis for tissue-specific functions of LPA and permit independent regulation of each subtype of LPA receptor.

Example 5

Cloning of Human Edg5 cDNA and Design and Preparation of Mammalian Expression Construct The human ortholog of rat H218/AGR16 was cloned by a combination of RT-PCR and RACE (rapid amplification of cDNA ends) methods. First, a human cDNA fragment was amplified with degenerate primers corresponding to the amino acid sequence LLAIAIER (SEQ ID NO: 6) (5'-ctcctg/cgccatc/tgciatc/tgaga/cg) (SEQ ID NO: 7) in the third transmembrane domain, and LLLLDSTC (SEQ ID NO: 8) (5'-cagc/gta/ca/ga/ca/gtccagc/gaga/gagc/ga) (SEQ ID NO: 9) in the sixth transmembrane domain of rat H218/AGR16. The cDNA template for the PCR reaction (35 cycles of 95° C. for 1 min, 55° C. for 1 min, 72° C. for 2 min on Stratagene's Robocycler) was reverse-transcribed products of polyA+ RNAs isolated from human neuroblastoma cell line SK-N-MC. A 400 bp product was obtained and sequenced, which has a DNA sequence 80% identical to the corresponding region of the rat H218/AGR16.

The rest of the cDNA sequence was then obtained by 5'- and 3'-RACE using RACE-ready cDNAs derived from human fetal brain (Marathon-ready human fetal brain cDNA, Clontech). The gene-specific primers in 5'- and 3'-RACE were derived from the 400 bp cDNA fragment (5'-gcaggacagtggagcaggcctcga (SEQ ID NO: 10) and 5'-ctctctacgccaagcattatgtgct, (SEQ ID NO: 11) respectively). The RACE reaction conditions were 35 cycles of 95° C. for 1 min, 60° C. for 1 min, 72° C. for 2 min on a Robocycler. RACE products were cloned into pCR2.0 (Invitrogene) and sequenced.

The sequences of RACE products, presumably located 5' and 3' to the original 400 bp PCR products, were highly-sinilar to the corresponding regions in rat H218/AGR16. The composite sequence of the RACE and the original 400 bp PCR products encoded a protein with an open reading frame for a 353 amino acid protein that is 92% identical to rat H218/AGR16. To obtain the full length cDNA, two primers corresponding to the immediate upstream and downstream of the coding sequence (5'-tcggatccccaccatgggcagcttgtactcg, (SEQ ID NO: 12) and 5'-atctagaccctcagaccaccgtgttgccctc (SEQ ID NO: 13), respectively) were used to amplify with Marathon-ready human fetal brain cDNA (95° C. for 1 min, 55° C. for 1 min, 72° C. for 2 min with pfu polymerase).

The resulting PCR product was cut with EcoRI and XbaI and cloned into pCDEF3 mammalian expression vector. The sequence of the cDNA confirmed that it is consistent with the composite sequence obtained from RACE and original PCR. Like its rat counterpart H218/AGR16, the human protein belongs to the Edg family of GPCRs, with amino acid sequence 43–44% identical to human SIP receptors Edg1 and Edg3, and 33–35% identical to LPA receptors Edg2 and Edg4. We concluded that it is the human ortholog of rat SIP receptor H218/AGR16, and therefore named it human Edg5.

Example 6

Tsup-1 Cell Expression of Edg Receptors

The Tsup-1 line of human CD4+8+3$^{low}$ T lymphoblastoma cells is a useful model for studies of the regulation of human T cell apoptosis induced by different immunologically-relevant stimuli. Goetzl et al., *J. Cell Biol.* 119:493 (1992). Tsup-1 cells also bear surface receptors for many endogenous mediators, that influence thymocyte and T cell apoptosis, including prostaglandins and neuropeptides. The semiquantitative reverse transcription-polymerase chain reaction method described below was used to assess the relative quantity of mRNA encoding each Edg receptor compared to that for glyceraldehyde 3-phosphate dehydrogenase (G3PDH) in unstimulated Tsup-1 cells.

The methodology employed is more fully described in Goetzl et al., *J. Immunol* (1999), supra. Briefly, total cellular RNA was extracted from suspensions of Tsup-1 cells by the TRlzol method (Gibco-BRL, Grand Island, N.Y.), and a Superscript kit (Gibco-BRL) was used for reverse transcription (RT) synthesis of cDNAs. Polymerase chain reaction (PCR) began with a "hot start" at 94° C. for 3 min, Taq DNA polymerase was added and amplification was carried out with 35 cycles of 30 s at 94° C., 2 min at 55° C. and 1 min at 72° C. Two uCi of [alpha-$^{32}$P] dCTP were added to some sets of reaction mixtures to allow quantification of mRNA encoding each Edg receptor relative to that of the standard G3PDH. Kaltreider et al., *Am J. Resp. Cell. Mol. Biol.* 16:133 (1996).

Oligonucleotide primer pairs were: 5'-dCCTGGCCAAGGTCATCCATGAC AAC (SEQ ID NO: 14) and 5'-dTGTCATACCAGGAAATGAGCTTGAC (SEQ ID NO: 15) for G3PDH; 5'-CTACACAAAAA GCT-TGGATCACTCA (SEQ ID NO: 16) and 5'-CGACCAA GTCTAGAGCGCTTCCGGT (SEQ ID NO: 17) for Edg-1 (1100 bp); 5'-dGCTCCACACACGGATGAGCAACC (SEQ ID NO: 18) and 5'-GTGGTC ATTGCTGTGAACTC-CAGC (SEQ ID NO: 19) for Edg-2 (621 bp); 5'-dCAAAATG AGGCCTTACGACGCCA (SEQ ID NO: 20) and 5'-dTCCCATTCTGAAGTGCTG CGTTC (SEQ ID NO: 21) for Edg-3 (701 bp); 5'-dAGCTGCACAGCC GCCTGCCC CGT (SEQ ID NO: 22) and 5'-dTGCTGTGCCATGCCAGACCTTGTC (SEQ ID NO: 23) for Edg-4 (775 bp); 5'-CTCTCTACGCC AAGCATTAT-GTGCT (SEQ ID NO: 24) and 5'-ATCTAGACCCT CAGACCACCGTGTTGCCCTC (SEQ ID NO: 25) for Edg-5 (500 bp); 5'-dAGTCCTCAAATCAT CCCA-CATCTGC (SEQ ID NO: 26) and 5'-dAAGTGGCACTCCT GTCTCGTAATC (SEQ ID NO: 27) for the type I vasoactive intestinal peptide receptor (VPAC1); and 5'-dTCC CAG-CAGGTGCCTGGCCTAC (SEQ ID NO: 28) and 5'-dCGAGCCTCTTGTACTGTGACTGGTC (SEQ ID NO: 29) for VPAC2.

PCR products were resolved by electrophoresis in a 2 g/100 ml agarose gel with ethidium bromide staining. G3PDH, VIPR and Edg R bands were cut from gels and solubilized for beta scintillation counting in 0.5 ml of sodium perchlorate solution at 55° C. for 1 h (EluQuick, Schleicher and Schuell, Keene, N.H.). Initially, the G3PDH cDNA templates in several different-sized portions of each sample were amplified to determine volumes that would result in G3PDH bands of equal intensity for each sample. Relative quantities of cDNA encoding each Edg receptor also were calculated by the ratio of radioactivity to that in the corresponding G3PDH band. Kaltreider et al., *Am. J. Resp. Cell. Mol. Biol.* 16:133 (1996). The following results were obtained, with ratio shown being the ratio of $^{32}$P in the VPAC or Edg receptor cDNA band to that in the G3PDH band:

TABLE 1

| Receptor | VPAC1 | VPAC2 | Edg-1 | Edg-2 | Edg-3 | Edg-4 | Edg-5 |
|---|---|---|---|---|---|---|---|
| Ratio | 0.03 | 0.28 | 0.06 | 0.46 | 0.28 | 0.76 | 0.12 |

The assay confirmed the known predominant expression of type II receptor for vasoactive intestinal peptide (VPAC2) and only marginal detectable mRNA for the type I (VPAC1). The levels of mRNA encoding Edg-2, Edg-3 and Edg-4 were determined to be as high or higher than that for VPAC2 (n=3), which has a mean density of 89,500/Tsup-1 cell as reported in Leppert et al., *FASEB J.* 9:1473 (1995). In contrast, the amounts of mRNA encoding Edg-1 and Edg-5 receptors were respectively just at the level of detection and less than half that of Edg-3.

Example 7

Effect of Apoptotic Stimuli on Edg Expression

Both LPA and S1P prevent apoptosis induced by anti-Fas antibody and a combination of anti-CD3 and anti-CD28 antibodies with differences only in lipid concentration-dependence. Goetzl et al., *J. Immunol* (1999), supra. In contrast, apoptosis evoked by C6-ceramide is suppressed significantly by S1P, but not by varying concentrations of LPA. An assay was performed to determine the effect of these various apoptotic stimuli on Edg receptor expression.

Human CD4+8+3$^{low}$ T lymphoblasts of the Tsup-1 line were cultured in RPMI-1640 medium (UCSF Cell Culture facility) containing 10% (v:v) fetal bovine serum (FBS), 100 U/ml of penicillin G, 100 ug/ml of streptomycin and 1 mM beta-mercaptoethanol (complete RPMI medium) at 37° C. in 5% $CO_2$ in air. Complete RPMI medium was added to cultures every 2–3 days to maintain a density of 0.5–1×10$^6$ Tsup-1 cells/ml. For all studies of the effects of LPA and S1P, batches of 3–5×10$^7$ Tsup-1 cells were conditioned in 30–50 ml of RPMI-1% FBS for 24 hours and RPMI-0.1% FBS for a minimum of 12 hours.

Briefly, after conditioning at low serum concentrations replicate suspensions of 5×10$^5$ Tsup-1 cells in 0.5 ml of RPMI-0.1% FBS were incubated in 24-well plastic plates (Falcon, Inc., Oxnard, Calif.) for 16 h at 37° C. in 5% $CO_2$ in air. Some wells were precoated overnight at 4° C. with 30 ng of anti-Fas antibody (Pharmingen, Inc., San Diego, Calif.), 0.2 ug of anti-CD2 antibody (Pharmirigen, Inc., San Diego, Calif.) or a combination of 0.5 ug each of anti-CD3 antibody (Caltag Laboratories, Inc., So. San Francisco, Calif.) and anti-CD28 antibody (Bristol-Myers Squibb Pharmaceutical Research Institute, Seattle, Wash.), and in others 5 uM C6 ceramide was the stimulus for apoptosis. LPA and S1P were dispersed 0.05 g/100 ml of faf-BSA in medium (fatty-acid free bovine serum albumin, from Sigma Chemical Co., St. Louis Mo.) The effects on Edg receptor expression were as follows:

TABLE 2

| Stimulus | Medium | Anti-Fas | Anti-CD2 | Anti-CD3 + Anti-CD28 | C6-Ceramide |
|---|---|---|---|---|---|
| Edg-2 | 0.47 | 0.39 | 0.31 | 0.35 | 0.05 |
| Edg-3 | 0.16 | 0.52 | 0.48 | 0.52 | 0.17 |
| Edg-4 | 0.63 | 0.57 | ND | 0.71 | 0.12 |

As above, the numbers shown correspond to the ratio of $^{32}$P in the Edg receptor cDNA band to that in the G3PDH band. Of the stimuli used to induce apoptosis in Tsup-1 cells, neither anti-Fas antibody nor antibodies to other surface protein antigens altered the levels of mRNA encoding Edg-2 or Edg-4 receptors. In contrast, a concentration of C6-ceramide that evoked maximal apoptosis reduced the apparent levels of Edg-2 and Edg-4 mRNA. The level of Edg-3 receptor mRNA determined by RT-PCR and radioactive PCR was increased by each of the apoptosis-inducing antibodies, but was unchanged by C6-ceramide.

Example 8

Antisense Suppression of Expression of Edg Receptors

The dependence of inhibition of activation-induced apoptosis by LPA and S1P on expression of Edg receptors by Tsup-1 cells was examined next by transfection of ligand-related combinations of antisense plasmids directed to the LPA receptors Edg-2 and -4 and the S1P receptors Edg-3 and -5.

Transfections of replicate suspensions of 4×10$^6$ cells in 2 ml of RPMI-2% FBS cultured as in Example 6 above were carried out by dropwise addition of a 250 ul preincubated mixture of 5 ug of antisense plasmid DNA, 0.2 ug of DNA of the REP 4 plasmid (InVitrogen, San Diego, Calif.) encoding hygromycin resistance and 15 ul of FuGENE 6 non-liposomal lipofection reagent (Boehringer-Mannheim Corp., Indianapolis, Ind.), incubation for 16–24 hours, and washing once and incubation in 4 ml of RPMI-10% FBS with 800 ug/ml of hygromycin for seven additional days. Then the surviving transfectants were washed and cultured in 4 ml of RPMI-0.1% FBS for 16 hours. Antisense plasmids containing full-length cDNA encoding Edg-2, -3, -4 and -5 receptors in the reverse orientation relative to promotors were constructed in the expression vectors pRc/CMV2 for Edg-2, pcDNA 3.1 for Edg-3 and Edg4 (InVitrogen, Inc., Carlsbad, Calif.) and pSV.SPORT1 for Edg-5 (GIBCO BRL, Gaithersburg, Md.) Control cells were sham-transfected with plasmids lacking these antisense inserts.

The principal assay for quantification of apoptosis was reliable and sensitive endlabeling of free 3'-OH groups of newly-generated nucleosomal DNA as described in Gavriela et al., *J. Cell. Biol.* 119:493 (1992). Briefly, cells from each well were pelleted at 200×g for 5 min at 4° C., resuspended in 0.5 ml of phosphate-buffered 4% formaldehyde, kept at room temperature for 10 minutes, re-pelleted, resuspended in 150 ul of 80% ethanol and immobilized and dried on poly-L-lysine precoated glass slides. Each slide was rehydrated in 20 mM Tris-130 mM NaCl (pH 7.6), and endogenous peroxidases were inactivated by treatment with 3% $H_2O_2$ in 90% methanol for 5 minutes at room temperature prior to endlabeling according to the procedures described in instructions for the Klenow-FragEL kit (Oncogene research Products-Calbiochem, Inc. La Jolla, Calif.). Percentage apoptosis was calculated from the number of Tsup-1 cells with stained nuclei of a total of 200 counted. Omission of Klenow fragment permitted assessment of those with residual endogenous peroxidase activity, that never exceeded 1%. The following results were obtained:

TABLE 3

| Antisense Pretreatment | LPA/S1P | anti-Fas antibody | percentage of control apoptosis* |
|---|---|---|---|
| Sham | LPA, 10$^{-9}$ M | + | 51 |
| Sham | LPA, 10$^{-8}$ M | + | 31 |
| Sham | S1P, 10$^{-9}$ M | + | 30 |
| Sham | S1P, 10$^{-8}$ M | + | 18 |
| Edg-2 & -4 | LPA, 10$^{-9}$ M | + | 69 |
| Edg-2 & -4 | LPA, 10$^{-8}$ M | + | 61 |
| Edg-2 & -4 | S1P, 10$^{-8}$ M | + | 22 |
| Edg-3 & -5 | S1P, 10$^{-9}$ M | + | 53 |
| Edg-3 & -5 | S1P, 10$^{-8}$ M | + | 39 |
| Edg-3 & -5 | S1P, 10$^{-8}$ M | + | 33 |

Each value is the mean of the results of two analyses corrected for the level in medium without anti-Fas antibody and expressed as a percentage of net apoptosis induced by anti-Fas antibody in medium alone without LPA or S1P= 100% These control levels of apoptosis evoked by anti-Fas antibody alone were 28% and 34%. As shown in Table 3, at 10$^{-9}$ M and 10$^{-8}$ M, LPA and SIP characteristically protected Tsup-1 cell sham transfectants from anti-Fas antibody-induced apoptosis. Protection from anti-Fas antibody-induced apoptosis by LPA was significantly less in Tsup-1 cells transfected with Edg-2 and -4 antisense plasmids, without a change in the effectiveness of SIP. Protection from anti-Fas antibody-induced apoptosis by S1P was significantly less in Tsup-1 cells transfected with Edg-3 and -5 antisense plasmids, without a change for LPA.

These data suggest that LPA and S1P effects on activation-induced apoptosis of Tsup-1 cells depend on expression of a relevant complement of the Edg receptors specific for each lysophospholipid ligand. Further studies described in Goetzl et al., *J. Immunol.* (1999), supra implicate alteration in the pro-apoptotic Bax regulatory protein (Penninger et al.,

*Adv.Inimunol.* 68:51 (1998) concentration as one of the mechanisms through which LPA and S1P protect some types of cells from apoptosis.

Example 9

BCC Expression of Edg Receptors

LPA and S1P stimulate cellular proliferation directly by eliciting the serum response factor (SRF) and ternary complex factor (FCT) transcription factors, which together bind to and activate the serum response element (SRE) in promoters of many immediate-early genes. Hill et al., *EMBO J*. 14:5037–42 (1995). In this study the estrogen receptor (ER)-positive MCF-7 cultured cell line of human breast cancer cells (ATCC # HTB-22) and the MDA-MB453 ER-negative line of breast cancer cells (ATCC # HTB-131) are shown to express several different functional Edg receptors and to proliferate in response to LPA and S1P.

The relative representation of each of the major Edg receptors was semi-quantified by RT-PCR as described in Example 6 supra. As shown in Table 4 below, the mRNA from both human BCC lines encoded similarly high levels the S1P receptor Edg-3, but had no detectable Edg-1 receptor. The ER-negative MDA-MB-453 BCCs had higher levels of mRNA encoding the LPA receptor Edg-2, whereas the,ER-positive MCF-7 BCCs had higher levels of mRNA for Edg-4 and Edg-5.

TABLE 4

| Cell Line | Edg-1 | Edg-2 | Edg-3 | Edg-4 | Edg-5 |
|---|---|---|---|---|---|
| MCF-7 | 0.00 | 0.04 ± 0.02 | 1.00 ± 0.08 | 0.70 ± 0.04 | 0.49 ± 0.09 |
| MDA-MB-453 | 0.00 | 0.17 ± 0.05 | 0.81 ± 0.08 | 0.43 ± 0.03 | 0.19 ± 0.07 |

Western blots performed with monoclonal mouse antihuman Edg antibodies confirmed BCC expression of Edg receptor proteins, with a predominace of Edg-3 receptor in both lines. However, the Western blots further demonstated that MCF-7 BCCs had higher levels of Edg-2 as well as Edg4 and Edg-5 protein than MDA-MB-453 BCCs, that was not predicted by results of mRNA analysis.

Briefly, hybridomas producing mouse monoclonal antibodies specific for substituent peptides of Edg-3 (amino acids 1–21), Edg4 (9–27) and Edg-5 (303–322) were generated from splenocytes of female Balb/c mice, that had been immunized first in multiple subcutaneous and intramuscular sites with 100 ug of keyhole limpet hemocyanin conjugate (Pierce Chemical Co., Rockford, Ill.) of the respective peptides in complete Freund's adjuvant, 3 weeks later and weekly for five additional weeks with 50 ug of the same conjugate in incomplete Freund's adjuvant, and then with 100 ug of unconjugated peptide alone intravenously 2 to 3 days before removal of the spleen (Antibody Solutions, Palo Alto, Calif.). Each monoclonal IgG was purified by protein A affinity-chromatography (Pierce Chemical Co.) and used to develop Western blots at 0.1–0.3 ug/ml. The cross-reactivity of each antibody with heterologous Edg proteins was less than 1%, as determined by Western blots of 0.1 to 100 ug of membrane proteins isolated from HTC rat hepatoma cells stably transfected with human Edg-2, -3, -4 or -5. A rabbit polyclonal antiserum to mouse Edg-2 was kindly provided by Dr. Jerold Chun (U.C. San Diego).

In the Western blots, replicate suspensions of $1 \times 10^7$ BCCs, that had been incubated without or with LPA or SIP for 16 hours, were washed three times with 10 ml of cold $Cal^{++}$ -and $Mg^{++}$ -free PBS, resuspended in 0.3 ml of cold 10 mM Tris-HCl (pH 7.4) containing a protease inhibitor cocktail (Sigma Chemical Co., St. Louis, Mo.), 0.12 M sucrose, and 5% glycerol (v:v). After homogenization with a Teflon pestle on ice for 2 min at 250 rpm, each sample was centrifuged at 400×g for 5 min at 4° C., and the supernatant was centrifuged at 300,000×g for 30 min at 4° C. Each 300,000×g pellet was resuspended in 0.2 ml of 10 mM Tris-HCl (pH 7.4) with 1% (v:v) Nonidet P-40, 5% glycerol and protease inhibitor cocktail, and re-homogenized at 4° C. for 2 hours prior to centrifugation again at 300,000×g. Aliquots of supernatant containing 1 to 100 ug of protein were mixed with 4× Laemmli's solution, heated to 100° C. for 3 min, and electrophoresed in an SDS-12% polyacrylamide gel for 20 min at 100 v and 1 ½ hours at 140 v, along with a rainbow pre-stained set of m w. markers (NEN-Dupont, Boston, Mass. or Amersham, Inc., Arlington Heights, Ill.). Proteins in each gel were transferred electrophoretically to a nitrocellulose membrane (Hybond, Amersham) for sequential incubation with 5 g % reconstituted nonfat milk powder to block unspecific sites, dilutions of mouse monoclonal anti-Edg receptor antibody and then horseradish peroxidase-labeled goal anti-mouse IgG, prior to development with a standard ECL kit (Amersham). Detailed data is shown in Goetzl et al., *FASEB J*. (1999), in press, herein incorporated by reference.

Example 10

Functional and Biochemical Responses of BCCs to LPA and S1P

Activation of SRE in the promoters of diverse growth-related genes is a fundamental characteristic of the growth-promoting potential of LPA and SIP. In this example, BCCs were transfected with an SRE-firefly luciferase construct and $\frac{1}{20}$ the amount of a Renilla luciferase-CMV construct as an internal standard for consistency of transfection. Signaling of transcription of growth-related genes, as assessed by prominent enhancement of SRE-coupled luciferase activity, was increased significantly by proliferation stimulating concentrations of LPA and SIP in both MCF-7 and MDA-MB-453 BCCS.

Briefly, layers of estrogen receptor positive MCF-7 (ATCC # HTB-22) and estrogen receptor-negative MDA-MB-453 (ATCC# HTB-13 1) human breast cancer cells (BCCs) were cultured in Dulbecco's minimal essential medium with 4.5 g/100 ml of glucose, 10% fetal bovine serum, 100 U/ml of penicillin G and 100 ug/ml of streptomycin (complete DMEM) to 100% confluence and relayered every 3 to 4 days to 25%–30% confluence. For the reporter assay, replicate suspensions of $1 \times 10^7$ MCF-7 and MDA-MB-453 BCCs in 1 ml of complete DMEM were cultured in 12-well plates for 24 hours to establish monolayers of 40% to 50% confluency. The monolayers were washed twice and covered with 1 ml of serum-free DMEM and lipotransfected with 100 ng/well of a serum response element (SRE) firefly luciferase reporter plasmid (described in An et al., *FEBS Letters* 412:279–82 (1997)) and 5 ng/well of pRL-CMV Renilla luciferase vector (Promega, Madison, Wis.) using FuGENE 6 (Boehringer-Mannheim Corp., Indianapolis, Ind.).

After 30 hours of incubation, medium was replaced with fresh serum-free DMEM and anti-IGFII mouse monoclonal antibody (Upstate Biotechnology, Inc., Lake Placid, N.Y.) or IgG1 isotype control were added followed in 2 hours by $10^{-10}$ M to $10^{-6}$ M LPA, SIP or other lipids in serum-free DMEM with 0.2 mg/ml of faf-BSA. After 4 h of incubation at 37° C., the luciferases were extracted in Reporter Lysis Buffer (Promega) and their activities quantified sequentially by luminometry using Luciferase Assay and Stop & Glo reagents (Promega), with integration of light emitted during the 15 sec after addition of each reagent (EG & G Berthold microplate luminometer, model LB96V). Firefly luciferase values were corrected for differences in apparent transfection efficiency if any Renilla luciferase signals in a set differed by more than 20% from the mean results for control unstimulated samples. LPA and S1P increased the mean levels of luciferase luninometric activity in ligand concentration-dependent relationships by maxima of up to 37-fold and 85-fold, respectively, in MCF-7 BCCs. Similar responses to the same concentrations of LPA and S1P were detected in MDA-MB-453 BCCs, where the respective mean maxima were 24-fold and 26-fold. Detailed data is shown in Goetzl. et al., supra.

Next, pharmacological inhibitors known to suppress one or more components of the pathways by which Edg receptors signal nuclear events were applied in BCCs transfected with the SRE-luciferase reporter. Wells were pretreated with pertussis toxin (PXIX, Calbiochem, Inc., La Jolla, Calif.) for 6 hours, recombinant Clostridium botulinum C3 ADP-ribotransferase (C3 exoenzyme, List Biological Laboratories, Inc., Campbell, Calif.), which ADP-ribosylates rho specifically, for 30 hours, and the MAP kinase kinase (MEK) inhibitor 2'-amino-3'-methoxyflavone (PD98059, Calbiochem) for 2 hours. As shown in Table 5 below, suppression of Gi protein activity by Pertussis toxin (PTX), the ras-MAPK pathway by a MEK inhibitor, and the rho pathway by C3 exoenzyme all substantially decreased nuclear signals from Edg receptors in both types of BCCs.

TABLE 5

|  | MCF-7 BCCs | | | MDA-MB-453 BCCs | | |
|---|---|---|---|---|---|---|
|  | PTX | MEK | C3 Exo | PTX | MEK | C3 Exo |
| LPA | 74 | 41 | 41 | 80 | 69 | 75 |
| S1P | 60 | 37 | 44 | 78 | 61 | 79 |

The above data represents percentage inhibition of the control responses to $10^{-7}$M LPA and $10^{-7}$ M S1P in serum-free DMEM without inhibitors (0% inhibition). The suppression of SRE-coupled reporter responses to LPA and S1P by Pertussis toxin and by inhibition of MEK and rho, in a pattern characteristic of signal transduction by Edg receptor, confirms the presence of functional Edg receptors in both BCC lines. Additionally, types I and II insulin-like growth factors (IGF-I and IGF-H) potently stimulate proliferation of many types of normal and malignant cells.

Stewart et al., *J. Biol, Chem* 265:21172–21178 (1990). Stimulation of MCF-7 BCC secretion of IGF-II by LPA and SIP was also inhibited by PIX, MEK inhibition and C3 exoenzyme sufficiently to implicate Gi and both the ras and rho pathways of signaling by the Edg receptors. Taken with the above results, this data suggests that Edg receptors transduce LPA and S1P enhancement of BCC growth both directly through the SRE and indirectly by enhancing the contribution of IGF-II.

All patent and literature references cited in the present specification are hereby incorporated by reference in their entirety.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid comprising:

(a) a nucleotide sequence encoding the amino acid sequence of SEQ ID NO: 1 or SEQ ID NO: 3; or (b) the nucleotide sequence of SEQ ID NO: 2 or SEQ ID NO: 4.

2. An isolated nucleic acid according to claim 1 operably linked to control sequences recognized by a host cell transformed with the nucleic acid.

3. An expression vector comprising the nucleic acid of claim 2.

4. A isolated host cell comprising the nucleic acid of claim 1.

5. A isolated host cell comprising the vector of claim 3.

6. A process for producing an Edg protein comprising culturing the host cell of claim 4 or claim 5 under conditions suitable for expression of the encoded protein.

7. A process according to claim 6 further comprising recovering said Edg protein.

8. The host cell of claim 5, wherein said expression vector is the Edg4/EF3 vector.

9. The host cell of claim 5, wherein said host cell is a Jurkat leukemic T cell.

10. The host cell of claim 5, wherein said host cell is a Tsup-1 human T lymphoblastoma cell.

11. The host cell of claim 5 wherein said host cell is further transformed with a reporter plasmid.

12. The host cell of claim 11, wherein said reporter plasmid is the SRE-luciferase reporter plasmid.

13. The cell of claim 4 in which the polynucleotide is selected from the group consisting of SEQ ID NO: 2 and SEQ ID NO: 4.

14. The cell of 13 which is selected from the group consisting of a Jurkat leukemic T cell and a Tsup-1 human T lymphoblastoma cell.

15. The cell of 13 which further comprises an exogenously supplied reporter nucleic acid.

16. The host cell of claim 15 in which the reporter nucleic acid is an SRE-luciferase reporter plasmid.

* * * * *

SEQUENCE LISTING

<160> NUMBER OF SEQ ID NOS: 29

<210> SEQ ID NO 1
<211> LENGTH: 382
<212> TYPE: PRT
<213> ORGANISM: Homo sapiens

<400> SEQUENCE: 1

Met Val Ile Met Gly Gln Cys Tyr Tyr Asn Glu Thr Ile Gly Phe Phe
 1               5                   10                  15

Tyr Asn Asn Ser Gly Lys Glu Leu Ser Ser His Trp Arg Pro Lys Asp
            20                  25                  30

Val Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60

Gln Pro Ile Tyr Tyr Leu Leu Gly Asn Leu Ala Ala Ala Asp Leu Phe
65                  70                  75                  80

Ala Gly Val Ala Tyr Leu Phe Leu Met Phe His Thr Gly Pro Arg Thr

-continued

```
                  85                  90                  95
Ala Arg Leu Ser Leu Glu Gly Trp Phe Leu Arg Gln Gly Leu Leu Asp
            100                 105                 110
Thr Ser Leu Thr Ala Ser Val Ala Thr Leu Leu Ala Ile Ala Val Glu
            115                 120                 125
Arg His Arg Ser Val Met Ala Val Gln Leu His Ser Arg Leu Pro Arg
            130                 135                 140
Gly Arg Val Val Met Leu Ile Val Gly Val Trp Val Ala Ala Leu Gly
145                 150                 155                 160
Leu Gly Leu Leu Pro Ala His Ser Trp His Cys Leu Cys Ala Leu Asp
                165                 170                 175
Arg Cys Ser Arg Met Ala Pro Leu Leu Ser Arg Ser Tyr Leu Ala Val
            180                 185                 190
Trp Ala Leu Ser Ser Leu Leu Val Phe Leu Leu Met Val Ala Val Tyr
            195                 200                 205
Thr Arg Ile Phe Phe Tyr Val Arg Arg Val Gln Arg Met Ala Glu
            210                 215                 220
His Val Ser Cys His Pro Arg Tyr Arg Glu Thr Thr Leu Ser Leu Val
225                 230                 235                 240
Lys Thr Val Val Ile Ile Leu Gly Ala Phe Val Val Cys Trp Thr Pro
                245                 250                 255
Gly Gln Val Val Leu Leu Leu Asp Gly Leu Gly Cys Glu Ser Cys Asn
            260                 265                 270
Val Leu Ala Val Glu Lys Tyr Phe Leu Leu Leu Ala Glu Ala Asn Ser
            275                 280                 285
Leu Val Asn Ala Ala Val Tyr Ser Cys Arg Asp Ser Glu Met Arg Arg
290                 295                 300
Thr Phe Arg Arg Leu Leu Cys Cys Ala Cys Leu Arg Gln Ser Thr Arg
305                 310                 315                 320
Glu Ser Val His Tyr Thr Ser Ser Ala Gln Gly Gly Ala Ser Thr Arg
                325                 330                 335
Ile Met Leu Pro Glu Asn Gly His Pro Leu Met Thr Pro Pro Phe Ser
                340                 345                 350
Tyr Leu Glu Leu Gln Arg Tyr Ala Ala Ser Asn Lys Ser Thr Ala Pro
            355                 360                 365
Asp Asp Leu Trp Val Leu Leu Ala Gln Pro Asn Gln Gln Asp
370                 375                 380
```

<210> SEQ ID NO 2
<211> LENGTH: 1734
<212> TYPE: DNA
<213> ORGANISM: Homo sapiens

<400> SEQUENCE: 2

| | | | | | |
|---|---|---|---|---|---|
| ggcacgaggc | gccgggccat | gggcctcgag | cccgccccga | accccgcga | gcccgccttg | 60 |
| tctgcggcgt | gactggaggc | ccagatggtc | atcatgggcc | agtgctacta | caacgagacc | 120 |
| atcggcttct | tctataacaa | cagtggcaaa | gagctcagct | cccactggcg | gcccaaggat | 180 |
| gtggtcgtgg | tggcactggg | gctgaccgtc | agcgtgctgg | tgctgctgac | caatctgctg | 240 |
| gtcatagcag | ccatcgcctc | caaccgccgc | ttccaccagc | ccatctacta | cctgctcggc | 300 |
| aatctggccg | cggctgacct | cttcgcgggc | gtggcctacc | tcttcctcat | gttccacact | 360 |
| ggtccccgca | cagcccgact | ttcacttgag | ggctggttcc | tgcggcaggg | cttgctggac | 420 |
| acaagcctca | ctgcgtcggt | ggccacactg | ctggccatcg | ccgtggagct | gcaccgcagt | 480 |

```
gtgatgtccg tgcagctgca cagccgcctg ccccgtggcc gcgtggtcat gctcattgtg      540
ggcgtgtggg tggctgccct gggcctgggg ctgctgcctg cccactcctg gcactgcctc      600
tgtgccctgg accgctgctc acgcatggca cccctgctca gccgctccta tttggccgtc      660
tgggctctgt cgagcctgtc tgtcttcctg ctcatggtgg ctgtgtacac ccgcattttc      720
ttctacgtgc ggcggcgagt gcagcgcatg cagagcatg tcagctgcca cccccgctac      780
cgagagacca cgctcagcct ggtcaagact gttgtcatca tcctgggggc gttcgtggtc      840
tgctggacac caggccaggt ggtactgctc ctggatggtt taggctgtga gtcctgcaat      900
gtcctggctg tagaaaagta cttcctactg ttggccgagg ccaactcact ggtcaatgct      960
gctgtgtact cttgccgaga tgctgagatg cgccgcacct tccgccgcct tctctgctgc     1020
gcgtgcctcc gccagtccac ccgcgagtct gtccactata catcctctgc ccagggaggt     1080
gccagcactc gcatcatgct tcccgagaac ggccacccac tgatgactcc acccttagc      1140 taccttgaac ttcagcggta cgcggcaagc aacaaatcca cagcccctga tgacttgtgg     1200
gtgctcctgg ctcaacccaa ccaacaggac tgactgactg caggacaag gtctggcatg      1260 gcacagcacc actgccaggc ctccccaggc acaccactct gcccagggaa tggggctttt     1320
gggtcatctc ccactgcctg ggggagtcag atgggtgca ggaatctggc tcttcagcca      1380
tctcaggttt aggggtttg taacagacat tattctgttt tcactgcgta tccttggtaa      1440
gccctgtgga ctggttaatg ctgtgtgatg ctgagggttt taaggtgggg agagataagg     1500
gctctctcgg gccatgctac ccggtatgac tgggtaatga ggacagactg tggacacccc     1560
atctacctga gtctgattct ttagcagcag agactgaggg gtgcagagtg tgagctggga     1620
aaggtttgtg gctccttgca gcctccaggg actggcctgt ccccaataga attgaagcag     1680
tccacgggga ggggatgata caaggagtaa acctttcttt acactcaaaa aaaa           1734
```

<210> SEQ ID NO 3
<211> LENGTH: 353
<212> TYPE: PRT
<213> ORGANISM: Homo sapiens

<400> SEQUENCE: 3

```
Met Gly Ser Leu Tyr Ser Glu Tyr Leu Asn Pro Asn Lys Val Gln Glu
 1               5                  10                  15

His Tyr Asn Tyr Thr Lys Glu Thr Leu Glu Thr Gln Glu Thr Thr Ser
            20                  25                  30

Arg Gln Val Ala Ser Ala Gly Ile Val Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Ser Ile Thr Leu Ser Ala Ser Val Gly Ser Leu Leu Ala Ile Ala Ile
        115                 120                 125

Glu Arg His Val Ala Ile Ala Lys Val Lys Leu Tyr Gly Ser Cys Lys
    130                 135                 140

Ser Cys Arg Met Leu Leu Leu Ile Gly Ala Ser Trp Leu Ile Ser Leu
```

-continued

```
             145                 150                 155                 160
    Val Leu Gly Gly Leu Pro Ile Leu Gly Trp Asn Cys Leu Gly His Leu
                     165                 170                 175
    Glu Ala Cys Ser Thr Val Leu Pro Leu Tyr Ala Lys His Tyr Val Leu
                     180                 185                 190
    Cys Val Val Thr Ile Phe Ser Ile Ile Leu Leu Ala Ile Val Ala Leu
                     195                 200                 205
    Tyr Val Arg Ile Tyr Cys Val Val Arg Ser Ser His Ala Asp Met Ala
                 210                 215                 220
    Ala Pro Gln Thr Leu Ala Leu Leu Lys Thr Val Thr Ile Val Leu Gly
    225                 230                 235                 240
    Val Phe Ile Val Cys Trp Leu Pro Ala Phe Ser Ile Leu Leu Leu Asp
                         245                 250                 255
    Tyr Ala Cys Pro Val His Ser Cys Pro Ile Leu Tyr Lys Ala His Tyr
                     260                 265                 270
    Phe Phe Ala Val Ser Thr Leu Asn Ser Leu Leu Asn Pro Val Ile Tyr
                 275                 280                 285
    Thr Trp Arg Ser Arg Asp Leu Arg Arg Glu Val Leu Arg Pro Leu Gln
                 290                 295                 300
    Cys Trp Arg Pro Gly Val Gly Val Gln Gly Arg Arg Arg Val Gly Thr
    305                 310                 315                 320
    Pro Gly His His Leu Leu Pro Leu Arg Ser Ser Ser Leu Glu Arg
                         325                 330                 335
    Gly Met His Met Pro Thr Ser Pro Thr Phe Leu Glu Gly Asn Thr Val
                     340                 345                 350
    Val

<210> SEQ ID NO 4
<211> LENGTH: 1122
<212> TYPE: DNA
<213> ORGANISM: Homo sapiens

<400> SEQUENCE: 4
atgggcagct tgtactcgga gtacctgaac cccaacaagg tccaggaaca ctataattat     60
accaaggaga cgctggaaac gcaggagacg acctcccgcc aggtggcctc ggccttcatc    120
gtcatcctct gttgcgccat gcaggagacg acctcccgcc aggtggcctc ggccttcatc    180
gtcatcctct gttgcgccat gtgtggtgaa aaccttctgg tgctcattgc ggtggcccga    240
aacagcaagt tccactcggc aatgtacctg tttctgggca acctggccgc ctccgatcta    300
ctggcaggcg tggccttcgt agccaatadd ttgctctctg gctctgtcac gctgaggctg    360
acgcctgtgc agtggtttgc ccgggagggc tctgcctcca tcacgctctc ggcctctgtc    420
ttcagcctcc tggccatcgc cattgagcgc acgtggcca ttgccaaggt caagctgtat    480
ggcagcgaca gagctgccg catgcttctg ctcatcgggg cctcgtggct catctcgctg    540
gtcctcggtg gcctgcccat ccttggctgg aactgcctgg ccacctcga ggcctgctcc    600 actgtcctgc ctctctacgc caagcattat gtgctgtgcg tggtgaccat cttctccatc    660
atcctgttgg ccatcgtggc cctgtacgtg cgcatctact gcgtggtccg ctcaagccac    720
gctgacatgg ccgccccgca gacgctagcc ctgctcaaga cggtcaccat cgtgctaggc    780
gtctttatcg tctgctggct gcccgccttc agcatcctcc ttctggacta tgcctgtccc    840
gtccactcct gcccgatcct ctacaaagcc cactactttt tcgccgtctc caccctgaat    900
tccctgctca cccccgtcat ctacacgtgg cgcagccggg acctgcggcg ggaggtgctt    960
```

```
cggccgctgc agtgctggcg gccgggggtg ggggtgcaag gacggaggcg ggtcgggacc    1020
ccgggccacc acctcctgcc actccgcagc tccagctccc tggagagggg catgcacatg    1080
cccacgtcac ccacgtttct ggagggcaac acggtggtct ga                       1122
```

<210> SEQ ID NO 5
<211> LENGTH: 375
<212> TYPE: DNA
<213> ORGANISM: Homo sapiens

<400> SEQUENCE: 5

```
gggccatggc tcgagccgcc ccgaccccccc gcgagcccgc cttgtctgcg gcgtgactgg      60
aggcccagat ggtcatcatg gccagtgct actacaacga gaccatcggc ttcttctata     120
acaacagtgg caaagagctc agctcccact ggcggcccaa ggatgtggtc gtggtggcac    180
tggggctgac cgtcagcgtg ctggtgctgc tgaccaatct gctggtcata gcagccatcg    240
cctccaaccg ccgcttccac cagcccatct actacctgct cggcaatctg gccgcggctg    300
acctcttcgc gggcgtggct acctcttcct catgttccac actggtcccc gcacagcccg    360
actttcactt gaggg                                                      375
```

<210> SEQ ID NO 6
<211> LENGTH: 8
<212> TYPE: PRT
<213> ORGANISM: combination of rat and human.

<400> SEQUENCE: 6

Leu Leu Ala Ile Ala Ile Glu Arg
 1               5

<210> SEQ ID NO 7
<211> LENGTH: 22
<212> TYPE: DNA
<213> ORGANISM: combination of rat and human.
<220> FEATURE:
<221> NAME/KEY: misc_feature
<222> LOCATION: (6)
<223> OTHER INFORMATION: The n at position 6 can be g or c.
<221> NAME/KEY: misc_feature
<222> LOCATION: (12)
<223> OTHER INFORMATION: The n at position 12 can be c or t.
<221> NAME/KEY: misc_feature
<222> LOCATION: (17)
<223> OTHER INFORMATION: The n at position 17 can be c or t.
<221> NAME/KEY: misc_feature
<222> LOCATION: (21)
<223> OTHER INFORMATION: The n at position 21 can be a or c.

<400> SEQUENCE: 7

```
ctcctngcca tngcatngag ng                                               22
```

<210> SEQ ID NO 8
<211> LENGTH: 8
<212> TYPE: PRT
<213> ORGANISM: combination of rat and human.

<400> SEQUENCE: 8

Leu Leu Leu Leu Asp Ser Thr Cys
 1               5

<210> SEQ ID NO 9
<211> LENGTH: 22
<212> TYPE: DNA
<213> ORGANISM: combination of rat and human.

```
<220> FEATURE:
<221> NAME/KEY: misc_feature
<222> LOCATION: (4)
<223> OTHER INFORMATION: The n at position 4 can be c or g.
<221> NAME/KEY: misc_feature
<222> LOCATION: (6)
<223> OTHER INFORMATION: The n at position 6 can be a or c.
<221> NAME/KEY: misc_feature
<222> LOCATION: (7)
<223> OTHER INFORMATION: The n at position 7 can be a or g.
<221> NAME/KEY: misc_feature
<222> LOCATION: (8)
<223> OTHER INFORMATION: The n at position 8 can be a or c.
<221> NAME/KEY: misc_feature
<222> LOCATION: (9)
<223> OTHER INFORMATION: The n at position 9 can be a or g.
<221> NAME/KEY: misc_feature
<222> LOCATION: (15)
<223> OTHER INFORMATION: The n at position 15 can be c or g.
<221> NAME/KEY: misc_feature
<222> LOCATION: (18)
<223> OTHER INFORMATION: The n at position 18 can be a or g.
<221> NAME/KEY: misc_feature
<222> LOCATION: (21)
<223> OTHER INFORMATION: The n at position 21 can be c or g.

<400> SEQUENCE: 9
cagntnnnnt ccagnagnag na                                        22

<210> SEQ ID NO 10
<211> LENGTH: 24
<212> TYPE: DNA
<213> ORGANISM: Homo sapiens

<400> SEQUENCE: 10
gcaggacagt ggagcaggcc tcga                                      24

<210> SEQ ID NO 11
<211> LENGTH: 25
<212> TYPE: DNA
<213> ORGANISM: Homo sapiens

<400> SEQUENCE: 11
ctctctacgc caagcattat gtgct                                     25

<210> SEQ ID NO 12
<211> LENGTH: 31
<212> TYPE: DNA
<213> ORGANISM: combination of rat and human.

<400> SEQUENCE: 12
tcggatcccc accatgggca gcttgtactc g                              31

<210> SEQ ID NO 13
<211> LENGTH: 31
<212> TYPE: DNA
<213> ORGANISM: combination of rat and human.

<400> SEQUENCE: 13
atctagaccc tcagaccacc gtgttgccct c                              31

<210> SEQ ID NO 14
<211> LENGTH: 25
<212> TYPE: DNA
<213> ORGANISM: Homo sapiens

<400> SEQUENCE: 14
cctggccaag gtcatccatg acaac                                     25
```

<210> SEQ ID NO 15
<211> LENGTH: 25
<212> TYPE: DNA
<213> ORGANISM: Homo sapiens

<400> SEQUENCE: 15
tgtcatacca ggaaatgagc ttgac                                          25

<210> SEQ ID NO 16
<211> LENGTH: 25
<212> TYPE: DNA
<213> ORGANISM: Homo sapiens

<400> SEQUENCE: 16
ctacacaaaa agcttggatc actca                                          25

<210> SEQ ID NO 17
<211> LENGTH: 25
<212> TYPE: DNA
<213> ORGANISM: Homo sapiens

<400> SEQUENCE: 17
cgaccaagtc tagagcgctt ccggt                                          25

<210> SEQ ID NO 18
<211> LENGTH: 23
<212> TYPE: DNA
<213> ORGANISM: Homo sapiens

<400> SEQUENCE: 18
gctccacaca cggatgagca acc                                            23

<210> SEQ ID NO 19
<211> LENGTH: 24
<212> TYPE: DNA
<213> ORGANISM: Homo sapiens

<400> SEQUENCE: 19
gtggtcattg ctgtgaactc cagc                                           24

<210> SEQ ID NO 20
<211> LENGTH: 23
<212> TYPE: DNA
<213> ORGANISM: Homo sapiens

<400> SEQUENCE: 20
caaaatgagg ccttacgacg cca                                            23

<210> SEQ ID NO 21
<211> LENGTH: 23
<212> TYPE: DNA
<213> ORGANISM: Homo sapiens

<400> SEQUENCE: 21
tcccattctg aagtgctgcg ttc                                            23

<210> SEQ ID NO 22
<211> LENGTH: 23
<212> TYPE: DNA
<213> ORGANISM: Homo sapiens

<400> SEQUENCE: 22

```
agctgcacag ccgcctgccc cgt                                              23

<210> SEQ ID NO 23
<211> LENGTH: 24
<212> TYPE: DNA
<213> ORGANISM: Homo sapiens

<400> SEQUENCE: 23
tgctgtgcca tgccagacct tgtc                                             24

<210> SEQ ID NO 24
<211> LENGTH: 25
<212> TYPE: DNA
<213> ORGANISM: Homo sapiens

<400> SEQUENCE: 24
ctctctacgc caagcattat gtgct                                            25

<210> SEQ ID NO 25
<211> LENGTH: 31
<212> TYPE: DNA
<213> ORGANISM: Homo sapiens

<400> SEQUENCE: 25
atctagaccc tcagaccacc gtgttgccct c                                     31

<210> SEQ ID NO 26
<211> LENGTH: 25
<212> TYPE: DNA
<213> ORGANISM: Homo sapiens

<400> SEQUENCE: 26
agtcctcaaa tcatcccaca tctgc                                            25

<210> SEQ ID NO 27
<211> LENGTH: 25
<212> TYPE: DNA
<213> ORGANISM: Homo sapiens

<400> SEQUENCE: 27
aagtggcact tcctgtctcg taatc                                            25

<210> SEQ ID NO 28
<211> LENGTH: 22
<212> TYPE: DNA
<213> ORGANISM: Homo sapiens

<400> SEQUENCE: 28
tcccagcagg tgcctggcct ac                                               22

<210> SEQ ID NO 29
<211> LENGTH: 25
<212> TYPE: DNA
<213> ORGANISM: Homo sapiens

<400> SEQUENCE: 29
cgagcctctt gtactgtgac tggtc                                            25
```